(12) United States Patent
Tao et al.

(10) Patent No.: US 10,562,944 B2
(45) Date of Patent: Feb. 18, 2020

(54) HERBICIDE-RESISTANT PROTEIN, ENCODING GENE AND USE THEREOF

(71) Applicant: BEIJING DABEINONG BIOTECHNOLOGY CO., LTD., Beijing (CN)

(72) Inventors: Qing Tao, Beijing (CN); Yechun Wu, Beijing (CN); Xiaoguang Niu, Beijing (CN); Derong Ding, Beijing (CN)

(73) Assignee: BEIJING DABEINONG BIOTECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/550,656

(22) PCT Filed: Feb. 2, 2016

(86) PCT No.: PCT/CN2016/073183
§ 371 (c)(1),
(2) Date: Aug. 11, 2017

(87) PCT Pub. No.: WO2016/127868
PCT Pub. Date: Aug. 18, 2016

(65) Prior Publication Data
US 2018/0244732 A1 Aug. 30, 2018

(30) Foreign Application Priority Data
Feb. 13, 2015 (CN) .......................... 2015 1 0078578

(51) Int. Cl.
*C07K 14/415* (2006.01)
*C12N 15/82* (2006.01)
*C12N 9/02* (2006.01)

(52) U.S. Cl.
CPC .......... *C07K 14/415* (2013.01); *C12N 9/0069* (2013.01); *C12N 15/8274* (2013.01); *C12N 15/8275* (2013.01); *C12N 15/8277* (2013.01)

(58) Field of Classification Search
None
See application file for complete search history.

(56) References Cited

U.S. PATENT DOCUMENTS

| 6,064,754 A * | 5/2000 | Parekh ............. G01N 27/44704 382/129 |
| 8,283,522 B2 * | 10/2012 | Wright ................. C12N 9/0071 800/300 |
| 8,916,752 B2 | 12/2014 | Wright et al. |

FOREIGN PATENT DOCUMENTS

| CN | 103361316 A | 10/2013 |
| CN | 103740664 A | 4/2014 |
| CN | 103740665 A | 4/2014 |
| CN | 103740666 A | 4/2014 |
| CN | 104611306 A | 5/2015 |
| CN | 104611308 A | 5/2015 |
| WO | WO 2005/107437 A2 | 11/2005 |
| WO | WO 2013/185036 A2 | 12/2013 |

OTHER PUBLICATIONS

International Search Report corresponding to Chinese application No. PCT/CN2016/073183 dated May 10, 2016.
Hogan et al., "Distribution of the tfdA Gene in Soil Bacteria That Do Not Degrade 2,4-Dichlorophenoxyacetic Acid (2,4-D)," Microbial Ecology, vol. 34, pp. 90-96 (1997). [Abstract Only].
Chinese Search Report corresponding to Chinese patent application No. 201510078578.3 dated Nov. 16, 2016.
First Chinese Office Action for Application No. 201510078578.3 dated Nov. 30, 2016.
Second Chinese Office Action for Application No. 201510078578.3 dated Jun. 5, 2017.
International Preliminary Report on Patentability and Written Opinion for Application No. PCT/CN2016/073183 dated Aug. 15, 2017.

\* cited by examiner

*Primary Examiner* — Eileen B O Hara
(74) *Attorney, Agent, or Firm* — Jenkins, Wilson, Taylor & Hunt, P.A.

(57) ABSTRACT

Involved is a herbicide-resistant protein, coding gene and use thereof. The herbicide-resistant protein comprises: (a) a protein consisting of an amino acid sequence shown in SEQ ID NO: 2; or (b) a protein with the activity of herbicide-resistance which is derived from the amino acid sequence in (a) by replacing and/or deleting and/or adding one or several amino acids in the same. The herbicide-resistant protein of this invention is especially suitable for expression in plants, with broad resistance spectrum to herbicides, especially to phenoxy auxin herbicides.

18 Claims, 5 Drawing Sheets

Specification includes a Sequence Listing.

1×2,4-D 1×MCPA
24DT21

1×2,4-D 1×MCPA
Wild type

24DT21

Wild type

24DT21　　　Control sequence　　　Wild-type
　　　　　　　　Water

24DT21　　　Control sequence　　　Wild-type
　　　　　　　　4X 2,4-D

HERBICIDE-RESISTANT PROTEIN, ENCODING GENE AND USE THEREOF

TECHNICAL FIELD

The present invention relates to a herbicide-resistant protein, encoding gene and use thereof, especially a 2,4-D-resistant protein, encoding gene and use thereof.

BACKGROUND

Weeds can quickly run out of the valuable nutrients in the soil which are necessary for the growth of crops and other target plants. At present, there are many types of herbicides for weeds control, among which is a particularly popular herbicide, glyphosate. Glyphosate-resistant crops have been developed, such as corn, soybean, cotton, beet, wheat, and rice, and the like. Thus, it is possible to spray glyphosate in the fields planted with glyphosate-resistant crops to control weeds without significant damage to the crops.

Glyphosate has been widely used all over the world for more than 20 years, resulting in the overdependence on the technology of glyphosate and glyphosate-tolerant crops. In addition, high selection pressure has been forced to the naturally more glyphosate-tolerant plants among the wild weed species or the plants which have developed resistance to glyphosate activity. It has reported that a few weeds have developed resistance to glyphosate, including broad-leaved weeds and gramineous weeds, such as Swiss ryegrass, *Lolium multiflorum*, *Eleusine indica*, *Ambrosia artemisiifolia*, *Conyza canadensis*, *Conyza bonariensis* and *Plantago lanceolata*. In addition, the weeds which are not the agricultural problem before the widespread use of glyphosate-tolerant crops also gradually prevailed, and are difficult to be controlled with glyphosate-tolerant crops. These weeds mainly exist along with (but not only with) broad-leaved weeds which are difficult to be controlled, such as species from *Amaranthus*, *Chenopodium*, *Taraxacum* and *Commelinaceae*.

In the area of glyphosate-resistant weeds or the weed species which are difficult to be controlled, growers can make up the weakness of the glyphosate through tank-mixing or using other herbicide which can control the omissive weeds. In most cases, a popular and effective tank-mixing partner used to control broad-leaved weeds is 2,4-dichlorophenoxyacetic acid (2,4-D). 2,4-D has been used to control broad-spectrum broad-leaved weeds more than 65 years under agriculture and non-crop conditions, and is still one of the most widely used herbicides in the world. The limit for further use of 2, 4-D is that its selectivity in dicotyledonous plants (such as soybeans or cotton) is very low. Therefore, 2,4-D is generally not used on (and generally not close to) sensitive dicotyledonous plants. In addition, the use of 2,4-D on gramineous crops is limited to a certain extent by the properties of the potential crop damage. The combination of 2,4-D and glyphosate has already been used to provide a stronger sterilization process before planting the no-till soybeans and cotton. However, due to the sensitivity of these dicotyledonous species to 2,4-D, these sterilization processes must be carried out 14 to 30 days before planting.

Same as MCPA, 2-methyl-4-chloropropionic acid and 2,4-D propionic acid, 2,4-De is also a phenoxy alkanoic acid herbicide. 2,4-D is used to selectively control broad-leaved weeds in many monocotyledonous crops such as corn, wheat and rice, without serious damage to the target crops. 2,4-D is a synthetic auxin derivative of which the function is to disorder the normal cytohormone homeostasis and to hinder the balance of controlled growth.

2,4-D shows different levels of selectivity on certain plants (for example, dicotyledonous plants are more sensitive than gramineous plants). Different 2,4-D metabolisms in different plants are one explanation for the different levels of selectivity. Plants usually metabolize 2, 4-D slowly. Thus, different activities of targeted points are more likely to explain different responses to 2, 4-D of plants. Plant metabolism of 2, 4-D is usually achieved through two steps of metabolism, i.e. the conjugation with amino acids or glucose following the hydroxylation in general.

As time goes on, the microbial populations have gradually developed effective, alternative pathways to degrade this particular foreign substance, which result in the complete mineralization of 2,4-D. Continuous application of herbicides on microbes can be used to select the microorganisms which use herbicides as carbon sources so as to make a competitive advantage in the soil. For this reason, 2,4-D was currently formulated with a relatively short soil half-life period and without obvious legacy effect on the subsequent crops, which promotes the application of 2, 4-D herbicide.

*Ralstonia eutropha* is one organism of which the ability for degrading 2,4-D has been widely studied. The gene encoding the enzyme in the first enzymatic step of mineralization pathway is tfdA. TfdA catalyzes the conversion of 2,4-D acid into dichlorophenol (DCP) through α-oxoglutarate-dependent dioxygenase reaction. DCP hardly has herbicide activity compared with 2,4-D. TfdA is used to introduce 2,4-D resistance into dicotyledonous plants which are usually sensitive to 2, 4-D (such as cotton and tobacco) in transgenic plants.

A number of tfdA type genes have been identified which encode proteins capable of degrading 2,4-D in the environment. Many homologs are similar with tfdA (amino acid identity >85%) and have similar enzyme activity with tfdA. However, not all proteins having structures such as TauD which have the function of degrading 2,4-D, and a large number of homologs have significantly lower identity (25-50%) with tfdA while contain characteristic residues associated with α-oxoglutarate-dependent dioxygenase Fe2+ dioxygenases. Therefore, the substrate specificities of these different dioxygenases are indefinite. A unique instance which has low homology (28% amino acid identity) with tfdA is rdpA from *Sphingobium herbicidovorans*. It has been shown that this enzyme catalyzes the first step in the mineralization of (R)-2,4-D propionic acid (and other (R)-phenoxy propionic acids) and 2, 4-D (phenoxyacetic acid).

With the emergence of glyphosate-resistant weeds and the expanded application of 2,4-D herbicide, it is necessary to introduce 2,4-D resistance into the target plants sensitive to 2,4-D. At present, no reports have been found about the expression levels of herbicide-resistant protein 24DT21 in plants and their herbicide tolerance.

SUMMARY

The purpose of the present invention is to provide a herbicide-resistant protein, coding gene and use thereof. The present invention is intentioned to provide a new 24DT21 gene which has higher herbicide tolerance in plants.

In order to accomplish said purpose, the present invention provides a herbicide-resistant protein, comprising:

(a) a protein consisting of an amino acid sequence shown in SEQ ID NO: 2; or (b) a protein with the activity of aryloxy alkanoate di-oxygenase which is derived from the amino acid sequence in (a) by replacing and/or deleting and/or adding one or several amino acids in the same.

In order to accomplish said purpose, the present invention provides a herbicide-resistant gene, comprising:

(a) a nucleotide sequence encoding said herbicide-resistant protein; or (b) a nucleotide sequence capable of hybridizing with the nucleotide sequence as defined in (a) under stringent conditions and encoding a protein with the aryloxy alkanoate di-oxygenase activity; or (c) the nucleotide sequence set forth in SEQ ID NO: 1.

The stringent conditions might be as follows: hybridization in 6×SSC (sodium citrate), 0.5% SDS (sodium dodecyl sulfate) solution at 65° C. and followed by washing membrane one time using 2×SSC, 0.1% SDS and 1×SSC, 0.1% SDS, respectively.

In order to accomplish said purpose, the present invention also provides an expression cassette, comprising said herbicide-resistant gene under the regulation of operably linked regulatory sequence.

In order to accomplish said purpose, the present invention further provides a recombinant vector, comprising said herbicide-resistant gene or said expression cassette.

In order to accomplish said purpose, the present invention provides a method for producing a herbicide-resistant protein, comprising:

obtaining the cells of a transgenic host organism containing the herbicide-resistance gene or the expression cassette;

cultivating the cells of the transgenic host organism under the conditions that allowing for the production of the herbicide-resistance protein;

recovering said herbicide-resistant protein.

Furthermore, the transgenic host organism includes plants, animals, bacteria, yeast, baculovirus, nematode or algae.

Preferably, the plant is soybean, cotton, corn, rice, wheat, beet or sugar cane.

In order to accomplish said purpose, the present invention also provides a method for extending the target range of herbicides, comprising: co-expressing the nucleotide encoding the herbicide-resistant protein or the herbicide-resistant protein encoded by the expression cassette with at least one second nucleotide that is different from said protein or the protein encoding by said expression cassette.

Furthermore, the second nucleotide encodes glyphosate-resistant protein, glufosinate-ammonium-resistant protein, 4-hydroxyphenylpyruvic acid dioxygenase, acetolactate synthase, cytochrome protein or protoporphyrinogen oxidase.

In present invention, the herbicide-resistant protein 24DT21 is expressed in a transgenic plant accompanied by the expressions of one or more glufosinate-resistant protein and/or glufosinate-ammonium-resistant proteins. Such a co-expression of more than one kind of herbicide-resistance protein in a same transgenic plant can be achieved by transforming and expressing the genes of interest in plants through genetic engineering. In addition, herbicide-resistant protein 24DT21 can be expressed in one plant (Parent 1) through genetic engineering operations and glyphosate-resistant protein and/or glufosinate-ammonium-resistant protein can be expressed in a second plant (Parent 2) through genetic engineering operations. The progeny plants expressing all genes of Parent1 and Parent 2 can be obtained by crossing Parent1 and Parent 2.

In order to accomplish said purpose, the present invention also provides a method for selecting transformed plant cells, comprising the steps of transforming multiple plant cells with the herbicide-resistant gene or the expression cassette and cultivating said cells at a herbicide concentration which allows the growth of the transformed cells expressing the herbicide-resistant gene or the expression cassette while kills the un-transformed cells or inhibits the growth of the un-transformed cells, wherein the herbicide is a phenoxy auxin.

In order to accomplish said purpose, the present invention also provides a method for controlling weeds, comprising the step of applying an effective amount of one or more herbicides to the field planted with crops which comprises said herbicide-resistant gene, said expression cassette or said recombinant vector. Preferably, the herbicide is a phenoxy auxin.

In order to accomplish said purpose, the present invention also provides a method for protecting plants from the damage caused by herbicides, comprising the step of introducing said herbicide-resistant gene, said expression cassette or said recombinant vector into plants, so as to make the resulted plants produce a certain quantity of herbicide-resistant protein sufficient to protect them from the damage caused by herbicides.

Preferably, the said herbicide is a phenoxy auxin or aryloxy phenoxy propionate and said plants are selected from the group consisting of soybean, cotton, corn, rice, wheat, beet and sugarcane.

In order to accomplish said purpose, the present invention also provides a method for controlling glyphosate-resistant weeds in a field planted with glyphosate-tolerant plants, comprising the step of applying an effective amount of one or more herbicides to the field planted with glyphosate-tolerant plants, wherein said glyphosate-tolerant plants comprise said herbicide-resistant gene, said expression cassette or said recombinant vector.

Preferably, said herbicide is a phenoxy auxin and said glyphosate-tolerant plant is monocotyledon or dicotyledon.

In order to accomplish said purpose, the present invention also provides a method for conferring crops with resistance to 2,4-D herbicides, comprising the steps of introducing said herbicide-resistant gene, said expression cassette or said recombinant vector into plants.

Preferably, said plant is soybean, cotton, corn, rice, wheat, beet or sugarcane.

In order to accomplish said purpose, the present invention also provides the use of herbicide-resistant proteins tolerant to phenoxy auxin herbicides, comprising:

(a) a protein consisting of the amino acid sequence shown in SEQ ID NO: 2; or (b) a protein with the activity of aryloxy alkanoate di-oxygenase which is derived from the amino acid sequence in (a) by replacing and/or deleting and/or adding one or more amino acids in the same.

The herbicide-resistant gene, said expression cassette or said recombinant vector is introduced into plants. The conventional methods used in present invention to introduce foreign DNA into plant cells include but are not limited to *Agrobacterium*-mediated transformation, Particle Bombardment, direct intake of DNA into protoplast, electroporation or silicon-mediated DNA introduction.

The 2,4-D resistant genes and subsequent resistant crops according to present invention provide a good choice to control glyphosate-resistant (or high tolerance or succession) broad-leaved weed species in crops. 2,4-D is a broad-spectrum, relatively cheap and powerful broad-leaved herbicides. If stronger crop tolerance in both dicotyledons and monocots could be provided, good efficacies could be provided for growers. 2,4-D-tolerant transgenic dicotylenons also have a higher flexibility in application time and administration amount. Another use of the 2,4-D herbicide-tolerance trait is that it could be used to prevent damages to normal sensitive crops such as 2,4-D drift, volatilization, transformation (or other remote movement phenomenon), misuse, destruction and the like. Various mixtures of different phenoxy auxins have been widely used to treat specific weed spectrum and environmental conditions in different areas. Using 24DT21 gene in plants can provide protections against broader-spectrum phenoxy auxin herbicide so as to improve the flexibility and controllable weed spectrum and provide protections to the full range of commercially available phenoxy auxin drift or other long distance phenoxy herbicides damages.

Phenoxy auxin herbicides are usually formulated as active acids, but some commercialized preparations are formulated as one of several corresponding ester preparations. Since general plant esterases in plants can convert these esters into active acids, they are also considered to be the substrates of 24DT21 enzyme in plants. Similarly, they can also be the organic or inorganic salts of the corresponding acids. When expressing chiral propionic acid, propionic acid salt or propionic ester herbicides, even if different CAS numbers may correspond to an optically pure compound. When denominating the herbicides, we still consider that racemic (R, S) or optically pure (R or S) enantiomer is a same herbicide. The possible dosage ranges can be those treated alone or combined with other herbicides in the applications in crops or non-crops.

It has been identified that the 24DT21 gene possesses the characteristics to allow the application of phenoxy auxin herbicide in plants after expressing the genetically engineered 24DT21 in plants, of which the inherent tolerance does not exist or is not enough to allow the application of these herbicides. In addition, 24DT21 gene can provide protection on phenoxy auxin herbicides when the natural tolerance is not enough to allow selectivity in plants. One, two or several phenoxy auxin herbicides can be continuously or tank-mixedly combined with it to treat plants only comprising 24DT21 gene. Dosage range of each phenoxy auxin herbicide used to control the broad-spectrum of dicotyledonous weeds ranges from 25 to 4000 g ae/ha, more generally from 100 to 2000 g ae/ha. Combination of these herbicides belonging to different chemical classes and having different action modes in a same field (continuously or tank-mixedly) can control most potential weeds which are intentioned to be controlled by the herbicides.

Glyphosate is widely used because it controls very broad spectrum of broad-leaved and gramineous weed species. However, the repeated use of glyphosate in the application of glyphosate-tolerant crops and non-crops has (and will continue to) selectively resulted in the succession of the weeds to species with more natural tolerance or glyphosate-resistant biotype. Most of the herbicide resistance management strategies recommend using effective amount of tank-mixed herbicide partners as a way to delay the appearance of resistant weeds. The herbicide partners provide the control of a same species but with different modes of action. The overlay of 24DT21 gene and glyphosate-tolerance trait (and/or other herbicide-tolerance traits) can provide the control of glyphosate-resistant weed species (broad-leaved weed species controlled by one or more phenoxy auxins) in glyphosate-tolerance crops by selectively applying glyphosate and phenoxy auxin (such as 2,4-D) on the same crops.

Applications of these herbicides might be the individual use of single herbicide composition in a tank mixture containing two or more herbicides with different action models simultaneously or sequentially (e.g. before planting, before seedling emergence or after seedling emergence) (interval time ranged from 2 hours to 3 months). Alternatively, compositions of any number of herbicides representing every class of compound could be used at any time (from within 7 months after planting to the time of harvest (or, as to a single herbicide, it refers to preharvest interval in which the shortest one is selected)).

Flexibility is very important in the control of broad-leaved weeds, i.e. application time, dosage of a single herbicide and the ability to control stubborn or resistant weeds. The dosage of glyphosate which overlays with glyphosate-resistant gene/24DT21 gene can range from 250 to 2500 g ae/ha; the dose of (one or more) phenoxy auxin herbicides can range from 25 to 4000 g ae/ha. The optimum combination of the application time depends on the specific conditions, species and the environment.

Herbicide formulations (such as esters, acids or salt formulas or soluble concentrates, emulsified concentrates or soluble solutions) and additives of tank-mixture (such as adjuvant or compatilizer) can significantly affect the weed control of a given herbicide or a combination of one or more kinds of herbicides. Any chemical combinations of any of above herbicides are comprised in the scope of this invention.

As well-known by one skilled in the art, the benefits of the combination of two or more action modes in improving the controlled weed spectrum and/or natural species with more tolerance or resistance weed species can be extended to chemicals capable of producing other herbicide tolerances besides glyphosate-tolerance in crops through artificial means (transgenic or non-transgenic). In fact, the following resistance characteristics can be encoded alone or be multiply overlayed so as to provide the ability to effectively control or prevent weeds from succession to any category of the above-mentioned herbicide resistances: glyphosate resistance (such as resistant plant or bacteria, EPSPS, GOX, GAT), glufosinate-ammonium resistance (such as PAT, Bar), acetolactate synthase (ALS) inhibitory herbicide resistance (such as imidazolidinone, sulfonylurea, triazole pyrimidine, sulphonanilide, pyrimidine thiobenzoate and other chemical resistance genes such as AHAS, Csrl, SurA etc.), bromoxynil resistance (such as Bxn), resistance to inhibitor of HPPD (4-Hydroxyphenylpyruvate dioxygenase), resistance to inhibitor of phytoene desaturase (PDS), resistance to photosystem II inhibitory herbicide (such as psbA), resistance to photosystem I inhibitory herbicide, resistance to protoporphyrinogen oxidase IX (PPO) inhibitory herbicide (such as PPO-1), phenylurea herbicide resistance (such as CYP76B1), dicamba degrading enzyme etc.

As to other herbicides, some of other preferable ALS inhibitors include triazolopyrimidine benzenesulfonamide (cloransulam-methyl, diclosulam, flumetsulam, metosulam and pyrimidino triazoles sulfonamide), pyrimidine thiobenzoate and flucarbazone. Some preferable HPPD inhibitors include mesotrione, isoxaflutole and sulcotrione. Some preferable PPO inhibitors include flumioxazin, butafenacil, carfentrazone, sulfentrazone and diphenyl oxide (such as aciflurofen, fomesafen, Lactofen and oxyfluorfen).

In addition, 24DT21 gene can be overlayed alone with one or more other input (such as insect resistance, fungus resistance or stress tolerance or output (such as the increased yield, improved oil mass, improved fiber quality) traits, or overlayed with one or more other input (such as insect resistance, fungus resistance or stress tolerance) or output (such as the increased yield, improved oil mass, improved fiber quality) traits after overlaying with other herbicide-resistant crop characteristics. Therefore, this invention can provide the ability to flexibly and economically control any number of agronomy pests and a complete agronomy solution to improve crop quality.

24DT21 gene in this invention can degrade 2,4-D, which is the basis of important herbicide-resistant crops and of the possibility of selection markers.

Almost all the herbicide combinations for broad-leaved weeds could be controlled by the transgenic expression of 24DT21gene. 24DT21 gene as an excellent herbicide tolerant crop trait can be overlayed with, for example, other herbicide-tolerant crop characteristics, such as glyphosate resistance, glufosinate-ammonium resistance, ALS inhibitor (such as imidazolidinone, sulfonylurea and triazolopyrimidine benzenesulfonamides) resistance, bromoxynil resistance, HPPD inhibitor resistance, PPO inhibitor resistance and the like) and insect resistance traits (Cry1Ab, Cry1F, Vip3, other *Bacillus thuringiensis* protein or insect-resistant protein derived from the non-*bacillus*). In addition, 24DT21 gene can be used as a selection marker to assist the selection of the primary transformant of plants genetically modified with another gene or genogroup.

Phenoxy alkanoate group can be used to introduce stable acid functional groups into herbicides. Acidic groups can import phloem activity by "acid capture" (the property required by herbicide effect) so as to be integrated into the new herbicides for activitity purpose. There are many commercially available and experimental herbicides as substrates of 24DT21. Therefore, tolerances to other herbicides can be obtained by using present invention.

The crop herbicide-tolerance trait of this invention can be used in a new combination with other crop herbicide-tolerance traits (including but not limited to glyphosate tolerance). Because of the newly acquired resistance or inherent tolerance to herbicides (such as glyphosate), the combinations of these traits produce new methods to control weed species. Therefore, in addition to crop herbicide-tolerance traits, present invention also includes new methods for controlling weeds by using herbicides, in which the said herbicide-tolerance is obtained through the enzyme produced by the transgenic crops.

The present invention can be applied to a variety of plants, such as *Arabidopsis*, tobacco, soybean, cotton, rice, corn and *brassica*. The present invention can also be applied to a variety of other monocotyledonous (such as gramineous herbage or grassy carpet) and dicotyledonous crops (such as alfalfa, clover and tree species, etc.). Similarly, 2, 4-D (or other 24DT21 substrates) can be applied more actively to gramineous crops with moderate tolerance, and the resulted tolerance of which traits are raised will provide growers the possibility to use these herbicides with more effective dosage and broader administration time without the risk of crop injury.

The genomes of plants, plant tissues or plant cells described in this invention refer to any genetic materials in the plants, plant tissues or plant cells, and include the nucleus, plasmids and mitochondrial genomes.

The "resistance" described herein is heritable, and allows the plants to grow and reproduce under the case that effective treatment is applied to the given plants using common herbicide. As acknowledged by one skilled in the art, even if a certain damage of the plant caused by herbicides is obvious, the plant can still be considered "resistance". The term "tolerance" described herein is broader than the term "resistance" and includes "resistance" and the improved ability of particular plant resistant to the various degree of damages induced by the herbicides which result generally in the damages of the wild type plants with the same genotypes under the same herbicide dosage.

As described herein, polynucleotides and/or nucleotides form a complete "gene" and encode proteins or polypeptides in the host cells of interest. It is easy for one skilled in the art to realize that the polynucleotides and/or nucleotides in the present invention can be under the control of the regulatory sequences of the target host.

As well known by one skilled in the art, DNA exists typically as double strands. In such an arrangement, one strand is complementary with the other, and vice versa. When DNA is replicated in plants, other complementary strands of DNA are also generated. Therefore, the polynucleotides exemplified in the sequence listing and complementary strands thereof are comprised in this invention. The "coding strand" generally used in the art refers to a strand binding with an antisense strand. To express a protein in vivo, one strand of the DNA is typically transcribed into a complementary strand of mRNA, which serves as the template of protein expression. In fact, a mRNA is transcribed from the "antisense" strand of DNA. "Sense strand" or "coding strand" contains a series of codons (codon is a triplet of nucleotides that codes for a specific amino acid), which might be read as open reading frames (ORF) to generate target proteins or peptides. RNA and PNA (peptide nucleic acid) which are functionally equivalent with the exemplified DNA were also contemplated in this invention.

Nucleic acid molecule or fragments thereof were hybridized with the herbicide-resistant gene under stringent condition in this invention. Any regular methods of nucleic acid hybridization or amplification can be used to identify the existence of the herbicide-resistant gene in present invention. Nucleic acid molecules or fragments thereof are capable of specifically hybridizing with other nucleic acid molecules under certain conditions. In present invention, if two nucleic acid molecules can form an antiparallel nucleic acid structure with double strands, it can be determined that these two molecules can hybridize with each other specifically. If two nucleic acid molecules are completely complementary, one of two molecules is called as the "complement" of the other one. In this invention, when every nucleotide of a nucleic acid molecule is complementary with the corresponding nucleotide of another nucleic acid molecule, it is identified the two molecules are "completely complementary". If two nucleic acid molecules can hybridize with each other so that they can anneal to and bind to each other with enough stability under at least normal "low-stringency" conditions, these two nucleic acids are identified as "minimum complementary". Similarly, if two nucleic acid molecules can hybridize with each other so that they can anneal to and bind to each other with enough stability under normal "high-stringency" conditions, it is identified that these two nucleic acids are "complementary". Deviation from "completely complementary" can be allowed, as long as the deviation does not completely prevent the two molecules to form a double-strand structure. A nucleic acid molecule which can be taken as a primer or a probe must have sufficiently complementary sequences to form a stable double-strand structure in the specific solvent at a specific salt concentration.

In this invention, basically homologous sequence refers to a nucleic acid molecule, which can specifically hybridize with the complementary strand of another matched nucleic acid molecule under "high-stringency" condition. The stringency conditions for DNA hybridization are well-known to one skilled in the art, such as treatment with 6.0×sodium chloride/sodium citrate (SSC) solution at about 45° C. and washing with 2.0×SSC at 50° C. For example, the salt concentration in the washing step is selected from 2.0×SSC and 50° C. for the "low-stringency" conditions and 0.2×SSC and 50° C. for the "high-stringency" conditions. In addition, the temperature in the washing step ranges from 22° C. for the "low-stringency" conditions to 65° C. for the "high-stringency" conditions. Both temperature and the salt concentration can vary together or only one of these two variables varies. Preferably, the stringency condition used in this invention might be as below. SEQ ID NO:1 is specifically hybridized in 6.0×SSC and 0.5% SDS solution at 65° C. Then the membrane was washed one time in 2×SSC and 0.1% SDS solution and 1×SSC and 0.1% SDS solution, respectively.

Therefore, certain herbicide-resistant sequence which can hybridize with SEQ ID NO: 1 under stringent conditions was comprised in this invention. These sequences were at least about 40%-50% homologous or about 60%, 65% or 70% homologous, even at least 75%, 80%, 85%, 90%, 91%, 92%, 93%, 94%, 95%, 96%, 97%, 98%, 99% or higher homologous to the sequences of present invention.

The present invention provides functional proteins. "Functional activity" (or "activity") as described herein means the activity of proteins/enzymes (alone or combined with other protein) in this invention to degrade herbicide or reduce the herbicide activity. The plants which produce the proteins of this invention preferably produce such an effective amount of proteins that, when treating plants with herbicides, the protein expression level is enough to provide the plants with complete or partial resistance or tolerance to herbicides (general dosage if there are no specific instructions). Herbicides are usually applied at the dosage capable of killing the target plants, normal dosage and concentration applied in the field. Preferably, plant cells and plants of this invention are protected from the growth inhibition or damage caused by herbicide treatment. The transformed plants and plant cells of the present invention preferably have resistance or tolerance to 2,4-D herbicides, which means that the transformed plants and plant cells can survive in the condition with effective amount of 2,4-D herbicides.

Genes and proteins described in the present invention include not only the specifically exemplified sequences, but also parts and/or fragments (including deletion(s) in and/or at the end of the full-length protein), variants, mutants, substitutes (proteins containing substituted amino acid(s)), chimeras and fusion proteins retaining the herbicide-resistant activity thereof. The said "variants" or "variation" refers to the nucleotide sequences encoding the same one protein or encoding an equivalent protein having herbicide-resistant activity. The said "equivalent protein" refers to the proteins that have the same or the substantially same bioactivity of herbicide-resistant activity as that of the claimed proteins.

The "fragment" or "truncation" of the DNA or protein sequences as described in this invention refers to a part or an artificially modified form thereof (e.g., sequences suitable for plant expression) of the original DNA or protein sequences (nucleotides or amino acids) involved in present invention. The sequence length of said sequence is variable, but it is long enough to ensure that the (encoded) protein is herbicide-resistant protein. In some cases (especially expression in plants), it is advantageous to use a truncated gene which encodes a truncated protein. The preferable, truncated gene usually encodes 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the whole protein.

Due to redundancy of the genetic codons, a variety of different DNA sequences can encode one same amino acid sequence. It is available for one skilled in the art to achieve substitutive DNA sequences encoding one same or substantially same protein. These different DNA sequences are comprised in this invention. The said "substantially same" sequence refers to a sequence in which certain amino acids are substituted, deleted, added or inserted, but herbicide-resistant activity thereof is not substantially affected, and also includes the fragments remaining the herbicide-resistant activity.

Substitution, deletion or addition of some amino acids in amino acid sequences in this invention is conventional technique in the art. Preferably, such an amino acid change includes: minor characteristics change, i.e. substitution of reserved amino acids which do not significantly influence the folding and/or activity of the protein; short deletion, usually a deletion of about 1-30 amino acids; short elongation of amino or carboxyl terminal, such as a methionine residue elongation at amino terminal; short connecting peptide, such as about 20-25 residues in length.

The examples of conservative substitution are the substitutions happening in the following amino acids groups: basic amino acids (such as arginine, lysine and histidine), acidic amino acids (such as glutamic acid and aspartic acid), polar amino acids (e.g., glutamine and asparagine), hydrophobic amino acids (such as leucine, isoleucine, and valine), aromatic amino acids (e.g., phenylalanine, tryptophan and tyrosine), and small molecular amino acids (such as glycine, alanine, serine and threonine and methionine). Amino acid substitutions generally not changing specific activity are well known in the art and have been already described in, for example, Protein edited by N. Neurath and R. L. Hill, published by Academic Press, New York in 1979. The most common substitutions are Ala/Ser, Val/Ile, Asp/Glu, Thu/Ser, Ala/Thr, Ser/Asn, Ala/Val, Ser/Gly, Tyr/Phe, Ala/Pro, Lys/Arg, Asp/Asn, Leu/Ile, Leu/Val, Ala/Glu and Asp/Gly, and reverse substitutions thereof.

Obviously, for one skilled in the art, such a substitution may happen outside of the regions which are important to the molecular function and still cause the production of active polypeptides. For the polypeptide of the present invention, the amino acid residues which are required for their activity and chosen as the unsubstituted residues can be identified according to the known methods of the art, such as site-directed mutagenesis or alanine-scanning mutagenesis (see, e.g. Cunningham and Wells, 1989, Science 244: 1081-1085). The latter technique is carried out by introducing mutations in every positively charged residue in the molecule and detecting the herbicide-resistant activity of the obtained mutation molecules, so as to identify the amino acid residues which are important to the activity of the molecules. Enzyme-substrates interaction sites can also be determined by analyzing its three-dimensional structure, which can be determined through some techniques such as nuclear magnetic resonance (NMR) analysis, crystallography, or photoaffinity labeling (see, for example, de Vos et al., 1992, Science 255:306-312; Smith, et al., 1992, J. Mol. Biol 224:899-904; Wlodaver, et al., 1992, FEBS Letters 309:59-64).

Therefore, amino acid sequences which have certain homology with the amino acid sequences set forth in SEQ ID No. 2 are also comprised in this invention. The sequence similarity/homology between these sequences and the sequences described in the present invention are typically more than 60%, preferably more than 75%, more preferably more than 80%, even more preferably more than 90% and more preferably more than 95%. The preferred polynucleotides and proteins in the present invention can also be defined according to more specific ranges of the homology and/or similarity. For example, they have a homology and/or similarity of 49%, 50% 51%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% with the sequences described in this invention.

Regulatory sequences described in this invention include but are not limited to a promoter, transit peptide, terminator, enhancer, leading sequence, introns and other regulatory sequences that can be operably linked to the said 24DT21gene.

The said promoter is a promoter expressible in plants, wherein said "a promoter expressible in plants" refers to a promoter which ensures that the coding sequences bound with the promoter can be expressed in plant cells. The promoter expressible in plants can be a constitutive promoter. The examples of promoters capable of directing the constitutive expression in plants include but are not limited to 35S promoter derived from Cauliflower mosaic virus, ubi promoter, promoter of GOS2 gene derived from rice and the like. Alternatively, the promoter expressible in plants can be a tissue-specific promoter, which means that the expression level directed by this promoter in some plant tissues such as in chlorenchyma, is higher than that in other tissues of the plant (can be measured through the conventional RNA test), such as the PEP carboxylase promoter. Alternatively, the promoter expressible in plants can be wound-inducible promoters as well. Wound-inducible promoters or promoters that direct wound-inducible expression manners refer to the promoters by which the expression level of the coding sequences can be increased remarkably compared with those under the normal growth conditions when the plants are subjected to mechanical wound or wound caused by the gnaw of insects. The examples of wound-inducible promoters include but are not limited to the promoters of genes of protease inhibitor of potatoes and tomatoes (pin I and pin II) and the promoters of corn protease inhibitor gene (MPI).

The said transit peptide (also called paracrine signal sequence or leader sequence) directs the transgenosis products into specific organelles or cellular compartments. For the receptor protein, the said transit peptide can be heterogeneous. For example, sequences encoding chloroplast transit peptide are used to lead to chloroplast; or 'KDEL' reserved sequence is used to lead to the endoplasmic reticulum or CTPP of the barley lectin gene is used to lead to the vacuole.

The said leader sequences include but are not limited to small RNA virus leader sequences, such as EMCV leader sequence (encephalomyocarditis virus 5' non coding region); Potato virus Y leader sequences, such as MDMV (Corn dwarf mosaic virus) leader sequence; human immunoglobulin heavy chain binding protein (BiP); untranslated leader sequence of the coat protein mRNA of Alfalfa Mosaic virus (AMV RNA4); Tobacco Mosaic virus (TMV) leader sequence.

The said enhancer includes but is not limited to Cauliflower Mosaic virus (CaMV) enhancer, Figwort Mosaic virus (FMV) enhancer, Carnations Etched Ring virus (CERV) enhancer, Cassava Vein Mosaic virus (CsVMV) enhancer, *Mirabilis* Mosaic virus (MMV) enhancer, Cestrum yellow leaf curling virus (CmYLCV) enhancer, Cotton leaf curl Multan virus (CLCuMV), *Commelina* yellow mottle virus (CoYMV) and peanut chlorotic streak mosaic virus (PCLSV) enhancer.

For the application of monocotyledon, the said introns include but are limited to corn hsp70 introns, corn ubiquitin introns, Adh intron 1, sucrose synthase introns or rice Act1 introns. For the application of dicotyledonous plants, the said introns include but are not limited to CAT-1 introns, pKANNIBAL introns, PIV2 introns and "super ubiquitin" introns.

The said terminators can be the proper polyadenylation signal sequences playing a role in plants. They include but are not limited to polyadenylation signal sequence derived from *Agrobacterium tumefaciens* nopaline synthetase (NOS) gene, polyadenylation signal sequence derived from protease inhibitor II (pin II) gene, polyadenylation signal sequence derived from peas ssRUBISCO E9 gene and polyadenylation signal sequence derived from α-tubulin gene.

The term "operably linked" described in this invention refers to the linking of nucleic acid sequences, which provides the sequences the required function of the linked sequences. The term "operably linked" described in this invention can be the linkage of the promoter with the sequences of interest, which makes the transcription of these sequences under the control and regulation of the promoter. When the sequence of interest encodes a protein and the expression of this protein is required, the term "operably linked" indicates that the linking of the promoter and said sequence makes the obtained transcript to be effectively translated. If the linking of the promoter and the coding sequence results in transcription fusion and the expression of the encoding protein are required, such a linking is generated to make sure that the first translation initiation codon of the obtained transcript is the initiation codon of the coding sequence. Alternatively, if the linking of the promoter and the coding sequence results in translation fusion and the expression of the encoding protein is required, such a linking is generated to make sure that the first translation initiation codon of the 5'untranslated sequence is linked with the promoter, and such a linking way makes the relationship between the obtained translation products and the open reading frame encoding the protein of interest meet the reading frame. Nucleic acid sequences that can be "operably linked" include but are not limited to sequences providing the function of gene expression (i.e. gene expression elements, such as a promoter, 5'untranslated region, introns, protein-coding region, 3'untranslated region, polyadenylation sites and/or transcription terminators); sequences providing the function of DNA transfer and/or integration (i.e., T-DNA boundary sequences, recognition sites of site-specific recombinant enzyme, integrase recognition sites); sequences providing selectable function (i.e., antibiotic resistance markers, biosynthetic genes); sequences providing the function of scoring markers; sequences assistant with the operation of sequences in vitro or in vivo (polylinker sequences, site-specific recombinant sequences) and sequences providing replication function (i.e. origins of replication of bacteria, autonomously replicating sequences, centromeric sequences).

This invention can confer new herbicide resistant trait(s) to the plants while adverse effects on phenotypes including yield are not observed. The plants of present invention can tolerate against 2×, 3×, 4× or 5× general application level of at least one subjected herbicide. The improvement of these resistance levels is in the scope of present invention. For example, it is possible to foreseeably optimize and further develop many kinds of known technologies in the art so as to increase the expression of a given gene.

In present invention, said herbicide-resistant protein is 24DT21 amino acid sequence as shown in SEQ ID NO: 2 of the sequence listing. Said herbicide-resistant gene is 24DT21 nucleotide sequence as shown in SEQ ID NO: 1 of the sequence listing. In order to be applied to plants, said herbicide-resistant gene also contains, besides coding region of the protein encoded by 24DT21 nucleotide sequence, other elements, such as encoding regions which encode transit peptides, the coding regions which encode selective marker proteins or the proteins which confer resistance to insect.

The herbicide-resistant protein 24DT21 as describe herein is tolerant to most phenoxy auxin herbicides. The genomes of the plants in present invention contain exogenous DNAs which contain 24DT21 nucleotide sequence. The plants are protected from the threat of herbicides by expressing effective amount of this protein. "Effective amount" refers to the amount which causes no damage or causes slight damage. At the same time, the plants should be morphologically normal, and could be cultivated under the common means for the consumption and/or generation of products.

The expression level of herbicide-resistance crystal proteins (ICP) in the plant materials can be determined using various methods described in this field, such as the method of quantifying mRNA encoding the herbicide-resistant protein in the tissue through using specific primers, or the method of quantifying the herbicide-resistant protein directly and specifically.

The present invention provides a herbicide-resistant protein, coding gene and use thereof with following advantages:

1. Strong herbicide-resistance activity. Herbicide-resistant protein 24DT21 of present invention is strongly resistant to herbicides, especially to phenoxy auxin herbicides, particularly 2,4-D.

2. Broad herbicide-resistance spectrum. The herbicide-resistant protein 24DT21 of present invention shows high resistance to a variety of plant phenoxy auxin herbicides, therefore it has broad application prospect on the plants.

The technical solutions of this invention will be further described through the appended figures and examples as following.

DETAILED DESCRIPTION OF THE EMBODIMENTS

The technical solution of herbicide-resistant protein, coding gene and use thereof in present invention will be further illustrated through the following examples.

Example 1: The Obtaining and Synthesis of 24DT21 Gene Sequence

1. Obtaining of 24DT21 Gene Sequence

Amino acid sequence of the 24DT21 herbicide-resistant protein (292 amino acids) was shown as SEQ ID NO: 2 in the sequence listing; the nucleotide sequence (879 nucleotides) encoding the corresponding amino acid sequence of 24DT21 herbicide-resistant protein (292 amino acids) was shown as SEQ ID NO: 1 in the sequence listing.

2. Synthesis of the Nucleotide Sequence as Described Above

The 24DT21 nucleotide sequence (shown as SEQ ID NO: 1 in the sequence listing) was synthesized by GenScript Co., Ltd. Nanjing, P. R. China; The synthesized 24DT21 nucleotide sequence (SEQ ID NO: 1) was linked with a SpeI restriction site at the 5' end, and a KasI restriction site at the 3' end.

Figure 1:
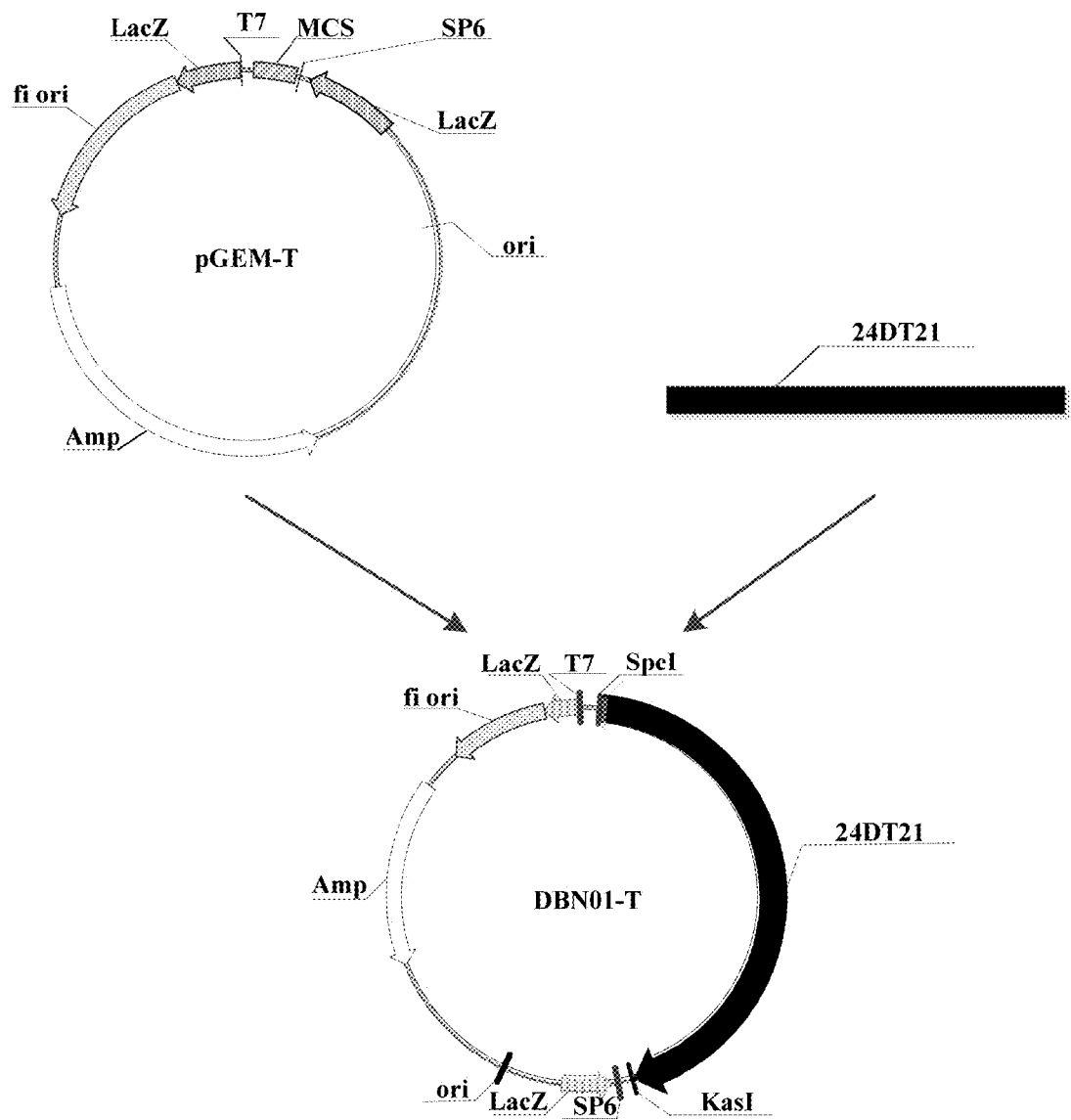
FIG. 1 shows the scheme to construct the recombinant cloning vector DBN01-T containing the 24DT21 nucleotide sequence used in the herbicide-resistant protein, coding gene and uses thereof in present invention.

Example 2: Construction of the Recombinant Expression Vectors of *Arabidopsis Thaliana* and Soybean 1. Construction of the Recombinant Cloning Vector DBN01-T Containing 24DT21 Nucleotide Sequence The synthesized 24DT21 nucleotide sequence was cloned into cloning vector pGEM-T (Promega, Madison, USA, CAT: A3600), to get recombinant cloning vector DBN01-T following the instructions of Promega pGEM-T vector, and the construction process was shown in FIG. 1 (wherein the Amp is ampicillin resistance gene; f1 is the replication origin of phage f1; LacZ is initiation codon of LacZ; SP6 is the promoter of SP6 RNA polymerase; T7 is the promoter of T7 RNA polymerase; 24DT21 is 24DT21 nucleotide sequence (SEQ ID NO: 1); MCS is multiple cloning sites).

The recombinant cloning vector DBN01-T was then transformed into *E. coli* T1 competent cell (Transgen, Beijing, China, the CAT: CD501) through heat shock method. The heat shock conditions were as follows: 50 μL of *E. coli* T1 competent cell and 10 μL of plasmid DNA (recombinant cloning vector DBN01-T) were incubated in water bath at 42° C. for 30 seconds. Then the *E. coli* cells were under shaking cultivation at 37° C. for 1 h (100 rpm in a shaking incubator) and then were grown on a LB plate (10 g/L Tryptone, 5 g/L yeast extract, 10 g/L NaCl, 15 g/L Agar and pH was adjusted to 7.5 with NaOH) coated on the surface with IPTG (Isopropyl thio-beta-D-galactose glucoside), X-gal (5-bromine-4-chlorine-3-indole-beta-D-galactose glucoside) and ampicillin (100 mg/L) overnight. The white colonies were picked out and cultivated in LB broth (10 g/L Tryptone, 5 g/L yeast extract, 10 g/L NaCl, 100 mg/L ampicillin and pH was adjusted to 7.5 with NaOH) at 37° C. overnight. The plasmids thereof were extracted using alkaline lysis method as follows: the bacterial liquid was centrifuged for 1 min at 12000 rpm, the supernatant was discarded and the pellet was resuspended in 100 μL in ice-chilled solution I (25 mM Tris-HCl, 10 mM EDTA (ethylenediaminetetraacetic acid) and 50 mM glucose, pH=8.0); then 200 μL of freshly prepared solution II (0.2 M NaOH, 1% SDS (sodium dodecyl sulfate)) was added and the tube was reversed 4 times, mixed and then put on ice for 3-5 minutes; 150 μL of cold solution III (3 M potassium acetate and 5 M acetic acid) was added, thoroughly mixed immediately and incubated on ice for 5-10 minutes; the mixture was centrifuged at 12000 rpm at 4° C. for 5 minutes, two volumes of anhydrous ethanol were added into the supernatant, mixed and then placed at room temperature for 5 minutes; the mixture was centrifuged at 12000 rpm at 4° C. for 5 minutes, the supernatant was discarded and the pellet was dried after washed with 70% ethanol (V/V); 30 μL TE (10 mM Tris-HCl, 1 mM EDTA, pH=8.0) containing RNase (20 μg/mL) was added to dissolve the precipitate; the mixture was incubated at 37° C. in a water bath for 30 min to digest RNA and stored at −20° C. for the future use.

After the extracted plasmids were confirmed with restriction enzymes SpeI and KasI, the positive clones were verified through sequencing. The results showed that said 24DT21 nucleotide sequence inserted into the recombinant cloning vector DBN01-T was the sequence set forth in SEQ ID NO: 1 in the sequence listing, indicating that 24DT21 nucleotide sequence was correctly inserted.

Figure 2:
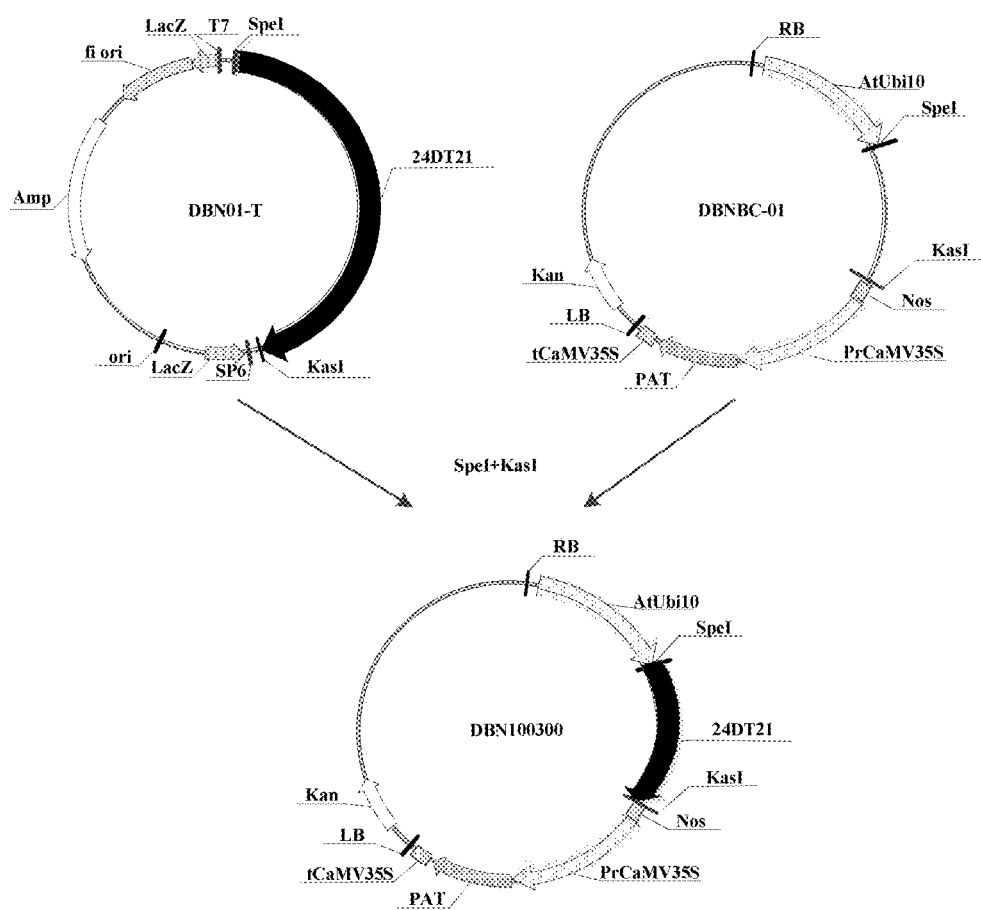
FIG. 2 shows the scheme to construct the recombinant expression vector DBN100300 containing 24DT21 nucleotide sequence used in the herbicide-resistant protein, coding gene and use thereof in present invention.

2. Constructing the Recombinant Expression Vectors DBN100300 of *Arabidopsis thaliana* and Soybean Containing 24DT21 Nucleotide Sequence The recombinant cloning vector DBN01-T and expression vector DBNBC-01 (Vector backbone: pCAMBIA2301, available from CAMBIA institution) were digested with restriction enzymes SpeI and KasI. The cleaved 24DT21 nucleotide sequence fragment was ligated between the restriction sites SpeI and KasI of the expression vector DBNBC-01 to construct the recombinant expression vector DBN100300. It is a well-known conventional method for one skilled in the art to construct expression vector through restriction enzyme digestion. The construction scheme was shown in FIG. 2 (Kan: kanamycin gene; RB: right border; AtUbi10: *Arabidopsis* Ubiquitin (Ubiquitin) 10 gene promoter (SEQ ID NO: 3); 24DT21: 24DT21 nucleotide sequence (SEQ ID NO: 1); Nos: terminator of nopaline synthetase gene (SEQ ID NO: 4); prCaMV35S: Cauliflower mosaic virus 35S promoter (SEQ ID NO:5); PAT: glufosinate acetyl transferase gene (SEQ ID NO:6); tCaMV35S: Cauliflower mosaic virus 35S terminator (SEQ ID NO: 7); LB: left border).

The recombinant expression vector DBN100300 was transformed into *E. coli* T1 competent cells with heat shock method as follows: 50 μL of *E. coli* T1 competent cell and 10 μL of plasmid DNA (recombinant expression vector DBN100300) were incubated in water bath at 42° C. for 30 seconds. Then the *E. coli* cells were under shaking cultivation at 37° C. for 1 hour (100 rpm in a shaking incubator) and then were grown on a LB solid plate (10 g/L Tryptone, 5 g/L yeast extract, 10 g/L NaCl, 15 g/L Agar and pH was adjusted to 7.5 with NaOH) containing 50 mg/L kanamycin at 37° C. for 12 hours. The white colonies were picked out and cultivated in LB broth (10 g/L Tryptone, 5 g/L yeast extract, 10 g/L NaCl, 50 mg/L kanamycin and pH was adjusted to 7.5 with NaOH) at 37° C. overnight. The plasmids thereof were extracted using alkaline lysis method.

After the extracted plasmids were confirmed with restriction enzymes SpeI and KasI, the positive clones were verified through sequencing. The results showed that the nucleotide sequence between restriction sites SpeI and KasI in the recombinant expression vector DBN100300 was the nucleotide sequence set forth in SEQ ID NO: 1 in the sequence listing, i.e. 24DT21 nucleotide sequence.

3. Constructing the Recombinant Expression Vectors DBN100300N of *Arabidopsis thaliana* and Soybean Containing a Control Sequence Following the process for constructing recombinant cloning vector DBN01-T comprising 24DT21 nucleotide sequence as described in part 1 of Example 2, recombinant cloning vector DBN01R-T containing control sequence was constructed by using control sequence (SEQ ID NO: 8). The positive clones were verified through sequencing. The results showed that the control nucleotide sequence inserted into the recombinant cloning vector DBN01R-T was the sequence set forth in SEQ ID NO: 8 in the sequence listing, indicating that control nucleotide sequence was correctly inserted.

Figure 3:
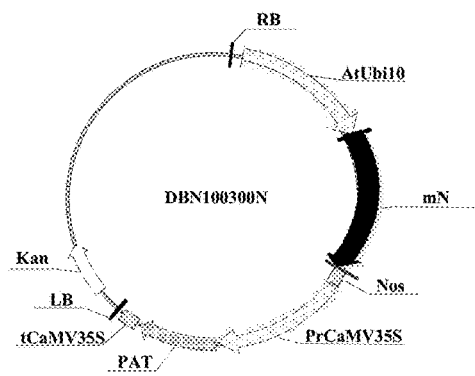
FIG. 3 shows the scheme to construct the recombinant expression vector DBN100300N containing control sequence used in the herbicide-resistant protein, coding gene and use thereof in present invention.

Following the process for constructing recombinant expression vector DBN100300 containing 24DT21 nucleotide sequence as described in part 2 of Example 2, recombinant expression vector DBN100300N containing control sequence was constructed using the control sequence and the structure of the vector was shown in FIG. 3 ((Vector backbone: pCAMBIA2301, available from CAMBIA institution); Kan: kanamycin gene; RB: right border; AtUbi10: *Arabidopsis* Ubiquitin (Ubiquitin) 10 gene promoter (SEQ ID NO: 3); mN: control sequence (SEQ ID NO: 8); Nos, terminator of nopaline synthetase gene (SEQ ID NO: 4); prCaMV35S: Cauliflower mosaic virus 35S promoter (SEQ ID NO:5); PAT: glufosynat acetyl transferase gene (SEQ ID NO:6); tCaMV35S: Cauliflower mosaic virus 35S terminator (SEQ ID NO: 7); LB: left border). The positive clones were verified through sequencing. The results showed that the control sequence inserted into the recombinant expression vector DBN100300N was the sequence set forth in SEQ ID NO: 8 in the sequence listing, indicating that control sequence was correctly inserted.

Example 3: Obtaining of the *Arabidopsis* Plant with Inserted 24DT21 Nucleotide Sequence 1. Transformation of *Agrobacterium tumefaciens* with Recombinant Expression Vectors The correctly constructed recombinant expression vectors DBN100300 and DBN100300N (control sequence) were transformed into *Agrobacterium* GV3101 following liquid nitrogen rapid-freezing method as follows: 100 μL *Agrobacterium* GV3101 and 3 μL plasmid DNA (recombinant expression vector) were put into liquid nitrogen for 10 minutes and then incubated in water bath at 37° C. for 10 minutes. Then the transformed *Agrobacterium* GV3101 cells were inoculated in LB broth and cultivated at 28° C., 200 rpm for 2 hours and spreaded on a LB plate containing 50 mg/L of rifampicin (Rifampicin) and 50 mg/L of kanamycin until positive mono colonies appeared. The positive mono colonies were picked up and cultivated and the plasmids thereof were extracted. Recombinant expression vector DBN100300 was verified with restriction enzymes PstI and SmaI and recombinant expression vector DBN100300N (control sequence) was verified with restriction enzymes SmaI and BglI. The results showed that the recombinant expression vectors DBN100300 and DBN100300N (control sequence) were correct in structure, respectively.

2. Obtaining Transgenic *Arabidopsis thaliana* Plants

The wild-type *Arabidopsis* seeds were suspended in 0.1% (w/v) agarose solution and kept at 4° C. for 2 days so as to meet the need for dormancy to ensure the synchronous germination of seeds. Vermiculite and horses dung were mixed together and irrigated wet with water underground. The soil mixture was dewatered for 24 hours. The pretreated seeds were cultivated in the soil mixture and covered with a moisturizing mask for 7 days. The seeds were germinated and the plants were cultivated in a greenhouse at a constant temperature of 22° C. with constant moisture of 40-50% and a long day condition with the light intensity of 120-150 $\mu mol/m^2s$ (16 hours of light/8 hours of darkness). The plants were irrigated with Hoagland nutrient solution at first and then with deionized water to keep the soil moist but not drenched.

Floral dip method was used to transform *Arabidopsis*. One or more YEP media containing 50 mg/L of kanamycin and 10 mg/L of rifampicin of 15-30 ml were inoculated with the selected *Agrobacterium* colonies as a pre-culture. The pre-culture was incubated at 28° C. and 220 rpm overnight. Each pre-culture was used to inoculate two cultures of 500 mL YEP media containing kanamycin (100 mg/L) and rifampicin (10 mg/L) and the cultures were incubated at 28° C. in a shaking incubator overnight. Cultures were centrifuged at 8700×g for 10 minutes at room temperature to precipate cells and the obtained supernatant was discarded. The cell pellets were gently re-suspended in 500 ml of permeable medium which contains ½×MS salts/vitamin B5, 10% (w/v) sucrose, 0.044 µM Benzylaminopurine (10 µL/L (1 mg/mL stock solution in DMSO)) and 300 µL/L Silvet L-77. About 1 month old plants were soaked in the medium for 15 seconds and the latest inflorescences were ensured to be submerged. Then plants were put down by side and covered (transparent or non-transparent) for 24 hours, then washed with water and placed vertically. The plants were cultivated at 22° C. in a light cycle of 16 hours of light/8 hours of darkness. Seeds were harvested after soaked for 4 weeks.

The newly harvested T1 seeds (24DT21 nucleotide sequence and control sequence) were dried at room temperature for 7 days. The seeds were cultivated in germination plates (26.5×51 cm), 200 mg T1 seeds (about 10000 seeds)/plate. The seeds have already been suspended in 40 mL of 0.1% (w/v) agarose solution and stored at 4° C. for 2 days to meet the need for dormancy to ensure the synchronous germination of seeds.

Vermiculite and horses dung were mixed together and irrigated wet with water underground and drained through gravity. The pretreated seeds (40 mL each one) were uniformly planted on the soil mixture by using pipette and covered with moisturizing mask for 4 to 5 days. The mask was removed 1 day before the initial transformant selection by spraying glufosinate-ammonium (selection of the co-transformed PAT gene) after germination.

On 7 days after planting (DAP) and 11 DAP respectively, the T1 plants (cotyledon stage and 2-4 leaves stage, respectively) were sprayed with 0.2% of Liberty herbicide solution (200 g ai/L glufosinate-ammonium) using DeVilbiss compressed air nozzle at a spraying volume of 10 mL/disc (703 L/ha) so as to provide effective amount of glufosinate-ammonium (280 g ai/ha) for each application. The survival plants (actively growing plants) were verified 4 to 7 days after the last spraying and transferred into the square pot (7 cm×7 cm) made from vermiculite and horses dung (3-5 plants per pot). The transplanted plants were covered with moisturizing mask for 3-4 days and placed in culture room at 22° C. or directly into the greenhouse as described above. Then the mask was removed and the plants were planted in greenhouse (22±5° C., 50±30% RH, 14 hours of lighting: 10 hours of darkness, minimum 500 µE/m2s1 natural light+ complement light) at least one day before testing the ability of 24DT21 to provide the resistance to phenoxy auxin herbicide.

Example 4: Herbicide Resistance Effect Test of the Transgenic *Arabidopsis*

24DT21 gene was used to transform *Arabidopsis* for the first time. At first, T1 transformants were selected from the background of un-transformed seeds, using glufosinate-ammonium selection scheme. About 20000 T1 seeds are screened among which 139 strains of T1 generation positive transformants (PAT gene) were identified, i.e. the transformation efficiency was about 0.7%. Herbicide resistance effect tests to 2,4-D dimethyl ammonium salt and agroxone of *Arabidopsis* T1 plants transformed with 24DT21 nucleotide sequence, control nucleotide sequence respectively and wild-type *Arabidopsis* plants were performed after 18 days of planting.

Figure 4:
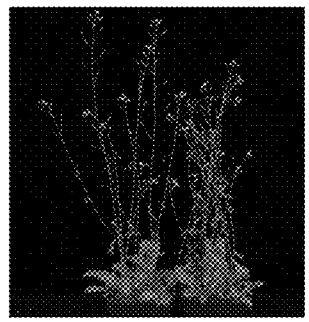
FIG. 4 shows the herbicide-resistant effect of the transgenic *Arabidopsis* T1 plant of the herbicide-resistant protein, coding gene and use thereof in present invention.
Figure 4:
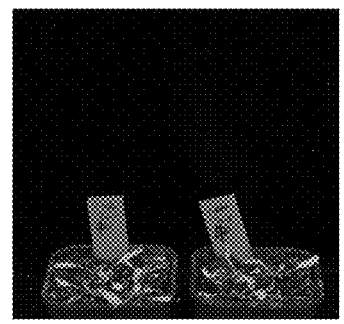
Figure 4:
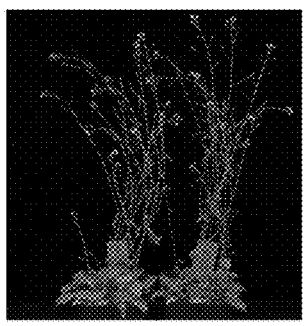
Figure 4:
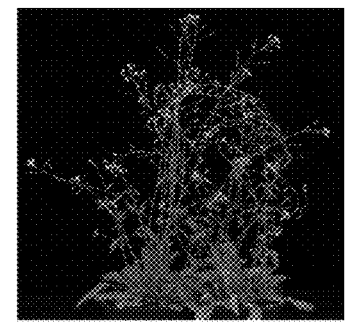

*Arabidopsis* T1 plants transformed with 24DT21 nucleotide sequence, control nucleotide sequence respectively and wild-type *Arabidopsis* plants were sprayed with 2,4-D dimethyl ammonium salt (560 g ae/ha, 1-fold concentration in field), agroxone (560 g ae/ha, 1-fold concentration in field) and blank solvent (water). Resistance conditions of the plants were counted 7 days and 14 days after spraying. Plants with growth conditions consistent with blank solvent (water) 7 days after spaying were classified as highly resistant plants; Plants with curly rosette leaves 7 days after spaying were classified as moderately resistant plants; Plants incapable of bolting 14 days after spaying were classified as low-resistant plants and the dead plants 14 days after spaying were classified as non-resistant plants. Because each *Arabidopsis* T1 plant is an independent transformation event, significant differences of individual T1 responses can be expected under a given dose. The results were shown in Table 1 and FIG. 4.

TABLE 1

Herbicide resistance results of transgenic *Arabidopsis* T1 plants

| Treatment | *Arabidopsis* genotype | High resistant | Moderate resistant | Low resistant | Non-resistant | Total |
|---|---|---|---|---|---|---|
| Blank solvent (H₂O) | 24DT21 | 32 | 0 | 0 | 0 | 32 |
| | Control | 32 | 0 | 0 | 0 | 32 |
| | Wild | 32 | 0 | 0 | 0 | 32 |
| 560 g ae/ha 2,4-D dimethyl ammonium salt (1x 2,4-D) | 24DT21 | 24 | 3 | 1 | 4 | 32 |
| | Control | 0 | 0 | 0 | 32 | 32 |
| | Wild | 0 | 0 | 0 | 32 | 32 |
| 560 g ae/ha agroxone (1xMCPA) | 24DT21 | 21 | 2 | 2 | 7 | 32 |
| | Control | 0 | 0 | 0 | 32 | 32 |
| | Wild | 0 | 0 | 0 | 32 | 32 |

For *Arabidopsis*, 560 g ae/ha of 2,4-D and agroxone is the effective dose to distinguish the sensitive plants from plants with average resistance. Results shown in Table 1 and FIG. 4 indicated that the 24DT21 gene confers herbicide resistance to individual *Arabidopsis* plants (only parts of the plants have the resistance because insertion sites of T1 generation plants are random. Therefore the resistant gene expression levels are different, resulting in the different levels of resistance), especially the phenoxy auxin herbicides. The wild-type *Arabidopsis* plants and *Arabidopsis* plants transformed with control sequence had no resistance to phenoxy auxin herbicide.

Example 5 Obtaining of the Soybean Plant with Inserted 24DT21 Nucleotide Sequence 1. Transformation of *Agrobacterium tumefaciens* with Recombinant Expression Vectors The correctly constructed recombinant expression vectors DBN100300 and DBN100300N (control sequence) were transformed into *Agrobacterium* LBA4404 (lnvitrgen, Chicago, USA, CAT: 18313-015) following liquid nitrogen rapid-freezing method, the transformation conditions are: *Agrobacterium* LBA4404 and 3 μL plasmid DNA (recombinant expression vector) were put into liquid nitrogen for 10 minutes and then incubated in water bath at 37° C. for 10 minutes. Then the transformed *Agrobacterium* LBA4404 cells were inoculated in LB broth and cultivated at 28° C., 200 rpm for 2 hours and spreaded on a LB plate containing 50 mg/L of rifampicin (Rifampicin) and 50 mg/L of kanamycin until positive mono colonies appeared. The positive mono colonies were picked up and cultivated and the plasmids thereof were extracted. Recombinant expression vectors DBN100300 was verified with restriction enzymes Sma I and Pst I and recombinant expression vector DBN100300N (control sequence) was verified with restriction enzymes Sma I and Bgl I. The results showed that the recombinant expression vectors DBN100300 and DBN100300N (control sequence) were correct in structure, respectively.

2. Obtaining Transgenic Soybean Plants

The cotyledonary node of wild-type soybean (Zhonghuang 13) was sterilely cultivated with the *Agrobacterium tumefaciens* described in Example 1 as to transfer the T-DNA of the recombinant expression vectors DBN100300 and DBN100300N described in Example 2 and 3 (containing promoter sequence of the *Arabidopsis thaliana* ubiquitin10 gene, 24DT21 nucleotide sequence, control sequence, Nos terminator, cauliflower mosaic virus 35S promoter, glufosinate acetyl transferase gene and cauliflower mosaic virus 35S terminator) into the soybean genome, soybean plants containing 24DT21 and control nucleotide sequences were obtained and at the same time wild-type soybean plant was taken as a control.

As to the *agrobacterium*-mediated transformation of soybean, in brief, mature soybean seeds were germinated in a soybean germination medium (3.1 g/L B5 salt, B5 vitamin, 20 g/L sucrose, 8 g/L agar and pH5.6) and cultivated at following conditions: temperature, 25±1° C.; photoperiod (light/darkness), 16/8 h. Fresh green aseptic soybean with bulging cotyledon node was obtained after 4-6 days of germination, cut off the hypocotyl which is 3-4 mm below the cotyledon node, cut the cotyledon longitudinally, and remove the terminal bud, the lateral bud and the seminal roots from the cotyledon, make a damage in the cotyledonary node with the back of a scalpel and bring *agrobacterium* suspension into contact with the damaged cotyledonary node tissues, wherein the *agrobacterium* can transfer the 24DT21 nucleotide sequence to the damaged cotyledonary node tissues (Step 1, infection step: in this step, preferably, the cotyledonary node tissue were immersed in *Agrobacterium* suspension ($OD_{660}$=0.5-0.8, infection medium (2.15 g/L MS salt, B5 vitamin, 20 g/L sucrose, 10 g/L glucose, 40 mg/L acetosyringone (AS), 4 g/L 2-(N-Morpholino) ethanesulfonic acid (MES), 2 mg/L zeatin (ZT), pH5.3)) to initiate the inoculation. Co-culture the cotyledonary node tissue with the *agrobacterium* for a period (3 days). (Step 2: co-cultivation step). Preferably, the colyledonary node tissues were cultured in a solid medium (4.3 g/L MS salt, B5 vitamin, 20 g/L sucrose, 10 g/L glucose, 4 g/L 2-(N-Morpholino) ethanesulfonic acid (MES), 2 mg/L zeatin, 8 g/L agar and pH5.6) after the infection. After this co-cultivation step, a selective "recovery" step can be preceded. In the "recovery" step, the recovery medium (3.1 g/L B5 salt, B5 vitamin, 1 g/L 2-(N-Morpholino) ethanesulfonic acid (MES), 30 g/L sucrose, 2 mg/L zeain (ZT), 8 g/L agar, 150 mg/L cephalosporin, 100 mg/L glutamic acid, 100 mg/L aspartic acid and pH5.6) contains at least one kind of known *Agrobacterium*-inhibiting antibiotics (cephalosporin) without the selective agent for plant transfectants (Step 3: recovery step). Preferably, the tissues were cultivated on solid medium culture containing antibiotics but without selective agent so as to eliminate *Agrobacterium* and to provide a recovery period for the infected cells. Then, the inoculated tissues were cultivated on a medium containing selective agent (glufosinate) and the transformed, growing callus was selected (Step 4: selection step). Preferably, the tissues were cultivated on a selective solid medium containing selective agent (3.1 g/L B5 salt, B5 vitamin, 1 g/L 2-(N-Morpholino) ethanesulfonic acid (MES), 30 g/L sucrose, 1 mg/L 6-benzyladenine (6-BAP), 8 g/L agar, 150 mg/L cephalosporin, 100 mg/L glutamic acid, 100 mg/L aspartic acid, 6 mg/L glufosinate, and pH5.6), resulting in the selective growth of the transformed cells. Then, callus regenerated into plants (Step 5: regeneration step), Preferably, the callus was cultivated on a solid medium containing selective agent (B5 differentiation medium and B5 rooting medium) to regenerate into plants.

The obtained resistant callus was transferred to said B5 differentiation medium (3.1 g/L B5 salt, B5 vitamin, 1 g/L 2-(N-Morpholino) ethanesulfonic acid (MES), 30 g/L sucrose, 1 mg/L zeatin (ZT), 8 g/L agar, 150 mg/L cephalosporin, 50 mg/L glutamic acid, 50 mg/L aspartic acid, 1 mg/L gibberellin, 1 mg/L auxin, 6 mg/L glufosinate and pH5.6) for cultivation and differentiation at 25° C. The differentiated seedlings were transferred to said B5 rooting medium (3.1 g/L B5 salt, B5 vitamin, 1 g/L 2-(N-Morpholino)ethanesulfonic acid (MES), 30 g/L sucrose, 8 g/L agar, 150 mg/L cephalosporin and 1 mg/L Indole-butyric acid (IBA)) and cultivated to about 10 cm in height at 25° C. Next, the seedlings were transferred to and cultivated in the greenhouse until fructification. In the greenhouse, the soybean plants were cultivated at 26° C. for 16 hours and at 20° C. for 8 hours every day.

3. Validating of Transgenic Soybean Plants with TaqMan Technique 100 mg of leaves from every transformed soybean plant (soybean plant transformed with 24DT21 nucleotide sequence or control nucleotide sequence) was taken as sample respectively. Genomic DNA thereof was extracted using DNeasy Plant Maxi Kit (Qiagen) and the copy number of 24DT21 gene was quantified through Taqman probe-based fluorescence quantitative PCR assay. Wild type soybean plant was taken as a control and analyzed according to the processes as described above. Experiments were carried out in triplicate and the results were the mean values.

The specific method for detecting the copy number of the PAT gene was described as follows:

Step 11: 100 mg of leaves from every transformed soybean plant (soybean plant transformed with 24DT21 nucleotide sequence or control nucleotide sequence, respectively) and wild type soybean plant was taken and grinded into homogenate in a mortar in liquid nitrogen respectively. It was in triplicate for each sample.

Step 12. the genomic DNAs of the samples above were extracted using DNeasy Plant Mini Kit (Qiagen) following the product instruction thereof;

Step 13. the genome DNA concentrations of the above samples were determined using NanoDrop 2000 (Thermo Scientific);

Step 14. the genome DNA concentrations were adjusted to the same range of 80-100 ng/μl;

Step 15. the copy numbers of the samples were quantified using Taqman probe-based fluorescence quantitative PCR assay, the quantified sample with known copy number was taken as a standard sample and the wild type soybean plant was taken as a control. It was carried out in triplicate for every sample and the results were the mean values. Primers and the probes used in the fluorescence quantitative PCR were shown as below.

The following primers and probes were used to detect the PAT nucleotide sequence:

```
Primer 1:
GAGGGTGTTGTGGCTGGTATTG
as shown in SEQ ID NO: 11 in the sequence list;

Primer 2:
TCTCAACTGTCCAATCGTAAGCG
as shown in SEQ ID NO: 12 in the sequence list;

Probe 1:
CTTACGCTGGGCCCTGGAAGGCTAG
as shown in SEQ ID NO: 13 in the sequence list;
```

PCR Reaction System:

| | |
|---|---|
| JumpStart ™ Taq ReadyMix ™ (Sigma) | 10 μL |
| 50 × primer/probe mixture | 1 μL |
| Genome DNA | 3 μL |
| Water (ddH$_2$O) | 6 μL |

Said 50×primer/probe mixture containing 45 μL of each primer (1 mM), 50 μL of the probe (100 μM) and 860 μL of 1 ×TE buffer and was stored in an amber tube at 4° C.

PCR Reaction Conditions:

| Step | Temperature | Time |
|---|---|---|
| 21 | 95° C. | 5 min |
| 22 | 95° C. | 30 s |
| 23 | 60° C. | 1 min |
| 24 | Back to Step 22, repeat 40 times | |

Data were analyzed using software SDS 2.3 (Applied Biosystems).

The experimental results showed that all the nucleotide sequence of the 24DT21 nucleotide sequence has been integrated into said detected soybean plants. Furthermore, all soybean plants transformed with 24DT21 nucleotide sequence or control sequence contained single copy of gene, respectively.

Example 6: Herbicide-Resistance Effect of the Transgenic Soybean Plants

Herbicide resistance effects tests to 2,4-D dimethyl ammonium salt and agroxone of soybean plants containing 24DT21 nucleotide sequence and control nucleotide sequence respectively and wild type soybean plants (stages V3-V4) were performed respectively.

Figure 5:
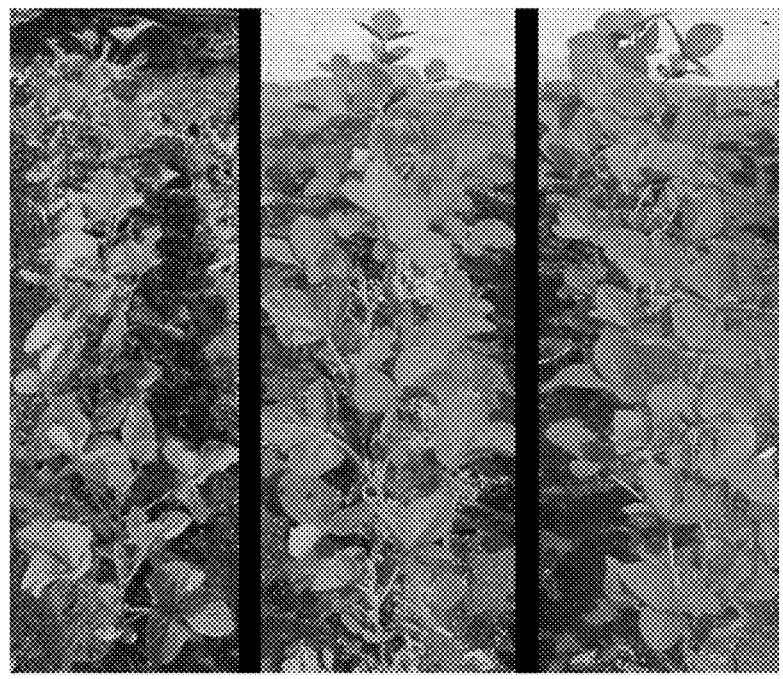
FIG. 5 shows the herbicide-resistant effect of the transgenic soybean $T_1$ plants of the herbicide-resistant protein, coding gene and use thereof in present invention.
Figure 5:

Soybean plants containing 24DT21 nucleotide sequence, control nucleotide sequence and wild type soybean plants were taken and spayed with 2,4-D dimethyl ammonium salt (2240 g ae/ha, four-folds concentration in field), agroxone (2240 g ae/ha, four-folds concentration in field) and blank solvent (water). Take statistics of the damage degree of each plant caused by herbicides according to the curling degree of leaves and the damage degree of growing point six hours (GHAT), two days (2DAT), seven days (7DAT) and 14 days (14DAT) after spraying respectively: if leaves are flat like wild-type leaves and the growing point is intact, the damage degree is 0%; if leaves curl up and wilt and the growing point is died, the damage degree is 100%. There are three strains contained a transferred 24DT21 nucleotide sequence (S1, S2 and S3), two strains contained a transferred control sequence (S4 and S5) and one wild-type strain (CK1) in total; select 10~15 plants from each strain for testing. The results were shown in Table 2 and FIG. 5.

TABLE 2

Experimental Results of the Herbicide Resistance of Genetically Modified Soybean T$_1$ Plants

| Treatment | Soybean genotype | Average damage % 6 HAT | Average damage % 2 DAT | Average damage % 7 DAT | Average damage % 14 DAT |
|---|---|---|---|---|---|
| Blank solvent (Water) | S1 | 0 | 0 | 0 | 0 |
| | S2 | 0 | 0 | 0 | 0 |
| | S3 | 0 | 0 | 0 | 0 |
| | S4 | 0 | 0 | 0 | 0 |
| | S5 | 0 | 0 | 0 | 0 |
| | CK1 | 0 | 0 | 0 | 0 |
| 2240 g ae/ha 2,4-D dimethyl ammonium salt (4 × 2,4-D) | S1 | 6 | 4 | 0 | 0 |
| | S2 | 11 | 4 | 0 | 0 |
| | S3 | 3 | 0 | 0 | 0 |
| | S4 | 46 | 76 | 96 | 100 |
| | S5 | 53 | 77 | 91 | 100 |
| | CK1 | 48 | 72 | 94 | 100 |
| 2240 g ae/ha agroxone (4 × MCPA) | S1 | 10 | 5 | 0 | 0 |
| | S2 | 16 | 11 | 6 | 0 |
| | S3 | 7 | 4 | 0 | 0 |
| | S4 | 38 | 69 | 87 | 100 |
| | S5 | 47 | 74 | 92 | 100 |
| | CK1 | 34 | 61 | 82 | 100 |

For soybean, 2240 g ae/ha of 2,4-D and agroxone is the effective dose to distinguish the sensitive plants from plants with average resistance. Results shown in Table 2 and FIG. 5 indicated that the 24DT21 gene confers herbicide resistance to individual soybean plants with high-level herbicide resistance, especially phenoxy auxin herbicides, while both wild-type soybean plants and soybean plants transformed with control sequence had no resistance to phenoxy auxin herbicide.

Figure 6:
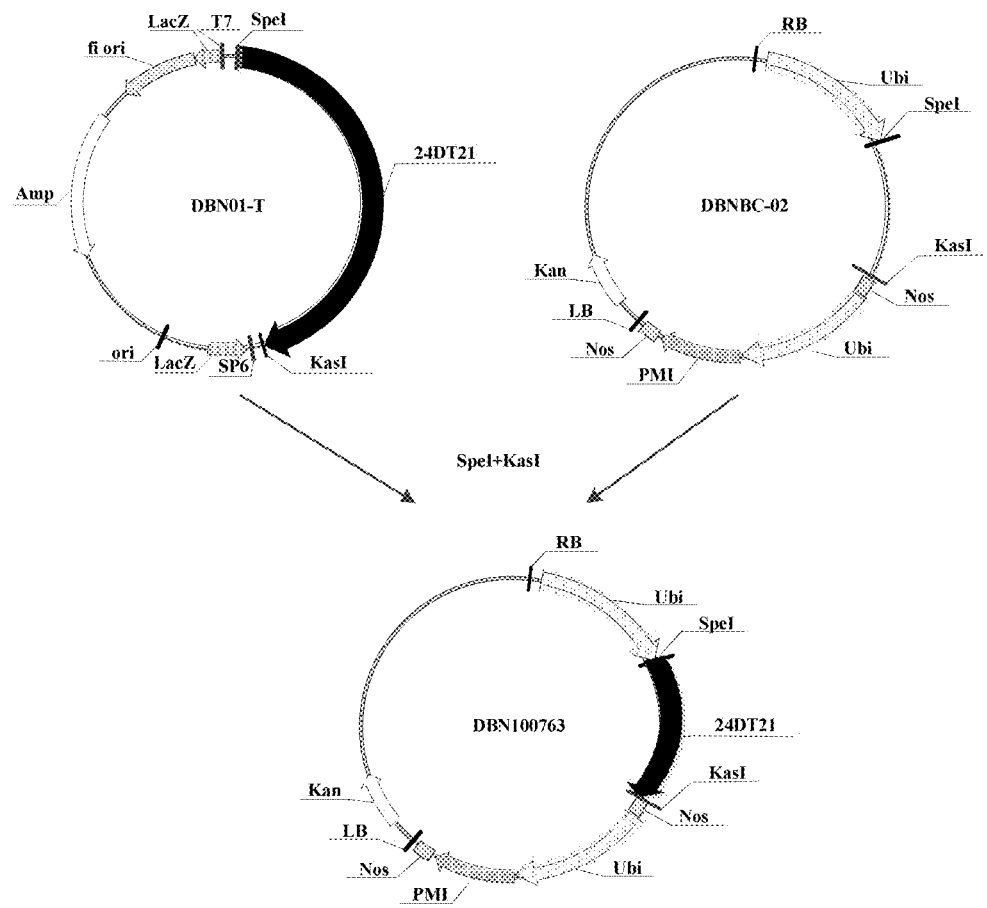
FIG. 6 shows the scheme to construct the recombinant expression vector DBN100763 containing 24DT21 nucleotide sequence used in the herbicide-resistant protein, coding gene and use thereof in present invention.

Example 7: Construction of Corn Recombinant Expression Vector and Transformation of *Agrobacterium* with Recombinant Expression Vector 1. Construction of the Corn Recombinant Expression Vector DBN100763 Containing 24DT21 Nucleotide Sequence The recombinant cloning vector DBN01-T and expression vector DBNBC-02 (Vector backbone: pCAMBIA2301, available from CAMBIA institution) were digested with restriction enzymes SpeI and KasI. The cleaved 24DT21 nucleotide sequence fragment was ligated between the restriction sites SpeI and KasI of the expression vector DBNBC-02 to construct the recombinant expression vector DBN100763. It is a well-known conventional method to construct expression vector through restriction enzyme digestion. SpeI and KasI restriction sites in the expression vector DBNBC-02 were also introduced using conventional enzyme digestion method. The construction scheme was shown in FIG. 6 (Kan: the kanamycin gene; RB: right border; Ubi: corn Ubiquitin (Ubiquitin) 1 gene promoter (SEQ ID NO: 9); 24DT21: 24DT21 nucleotide sequence (SEQ ID NO: 1); Nos: terminator of nopaline synthetase gene (SEQ ID NO: 4); PMI: phosphomannose isomerase gene (SEQ ID NO: 10); LB: left border).

The recombinant expression vector DBN100763 was transformed into E. coli T1 competent cells with heat shock method as follows: 50 µL of E. coli T1 competent cell and 10 µL of plasmid DNA (recombinant expression vector DBN100763) were incubated in water bath at 42° C. for 30 seconds. Then the E. coli cells were incubated in shaking cultivation at 37° C. for 1 hour (100 rpm in a shaking incubator) and then were grown on a LB solid plate (10 g/L Tryptone, 5 g/L yeast extract, 10 g/L NaCl, 15 g/L Agar and pH was adjusted to 7.5 with NaOH) containing 50 mg/L kanamycin (kanamycin) at 37° C. for 12 hours. The white colonies were picked out and cultivated in LB broth (10 g/L Tryptone, 5 g/L yeast extract, 10 g/L NaCl, 50 mg/L kanamycin and pH was adjusted to 7.5 with NaOH) at 37° C. overnight. The plasmids thereof were extracted using alkaline lysis method. After the extracted plasmids were confirmed with restriction enzymes SpeI and KasI, the positive clones were verified through sequencing. The results showed that the nucleotide sequence between restriction sites SpeI and KasI in the recombinant expression vector DBN100763 was the nucleotide sequence set forth in SEQ ID NO: 1 in the sequence listing, i.e. 24DT21 nucleotide sequence.

2. Construction of the Corn Recombinant Expression Vector DBN100763N Containing Control Nucleotide Sequence Following the process for constructing recombinant cloning vector DBN01-T containing 24DT21 nucleotide sequences described in part 1 of Example 2, recombinant cloning vector DBN02R-T containing control sequence was constructed by using control sequence (SEQ ID NO: 8). The positive clones were verified through sequencing. The results showed that the control nucleotide sequence inserted into the recombinant cloning vector DBN02R-T was the sequence set forth in SEQ ID NO: 8 in the sequence listing, indicating that control nucleotide sequence was correctly inserted.

Figure 7:
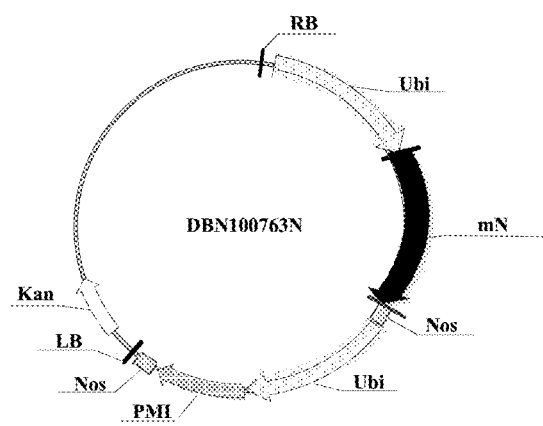
FIG. 7 shows the scheme to construct the recombinant expression vector DBN100763N containing control sequence used in the herbicide-resistant protein, coding gene and use thereof in present invention.

Following the process for constructing recombinant expression vector DBN100763 containing 24DT21 nucleotide sequence as described in part 1 of example 7, recombinant expression vector DBN100763N containing natural sequence was constructed by using the control sequence and the construction process was shown in FIG. 7 (Vector backbone: pCAMBIA2301, available from CAMBIA institution); Kan: kanamycin gene; RB: right border; ZmUbi1: corn Ubiquitin (ubiquitin) 1 gene promoter (SEQ ID NO: 9); mN: control sequence (SEQ ID NO: 8); Nos: terminator of nopaline synthetase gene (SEQ ID NO: 4); PMI: phosphomannose-isomerase gene (SEQ ID NO: 10); LB: left border). The positive clones were verified through sequencing. The results showed that the control sequence inserted into the recombinant expression vector DBN100763N was the sequence set forth in SEQ ID NO: 8 in the sequence listing, indicating that the control nucleotide sequence was correctly inserted.

3. Transformation of Agrobacterium tumefaciens with Corn Recombinant Expression Vectors The correctly constructed recombinant expression vectors DBN100763 and DBN100763N (control sequence) were transformed into Agrobacterium LBA4404 (Invitrgen, Chicago, USA, CAT: 18313-015) following liquid nitrogen rapid-freezing method as follows: 100 µL Agrobacterium LBA4404 and 3 µL plasmid DNA (recombinant expression vector) were put into liquid nitrogen and kept for 10 minutes and then incubated in water bath at 37° C. for 10 minutes. Then the transformed Agrobacterium LBA4404 cells were inoculated in LB tube and cultivated at 28° C., 200 rpm for 2 hours and spreaded on a LB plate containing 50 mg/L of rifampicin (Rifampicin) and 50 mg/L of kanamycin until positive mono colonies appeared. The positive mono colonies were picked up and cultivated and the plasmids thereof were extracted. Recombinant expression vector DBN100763 was verified with restriction enzymes Pst I and Xho I and DBN100763N (control sequence) was verified with restriction enzymes Sma I and Bgl I. The results showed that the recombinant expression vectors DBN100763 and DBN100763N (control sequence) were correct in structures, respectively.

Example 8: Obtaining and Verification of the Transgenic Corn Plants with Inserted 24DT21 Nucleotide Sequence According to the conventional Agrobacterium transformation method, the corn cultivar Zong 31 (Z31) was cultivated in sterilized conditions and the young embryo was co-cultivated with the Agrobacterium strains constructed in part 3 of Example 7 so as to introduce T-DNAs in the recombinant expression vectors DBN100763 and DBN100763N (control sequence) constructed in part 1 and 2 of Example 7 (including corn Ubiquitin 1 gene promoter sequence, 24DT21 nucleotide sequence, control nucleotide sequence, PMI gene and Nos terminator sequence) into the corn genome. Corn plants containing 24DT21 nucleotide sequence and control nucleotide sequence respectively were obtained and at the same time wild type corn plant was taken as a control.

As to the Agrobacterium-mediated transformation of corn, in brief, immature corn young embryo was isolated from corns and contacted with Agrobacterium suspension, in which the Agrobacterium can deliver the 24DT21 nucleotide sequence into at least one cell of one young embryo. (Step 1: infection step). In this step, preferably, young embryo was immersed in Agrobacterium suspension (OD660=0.4~0.6, infection medium (4.3 g/L of MS salt, MS vitamins, 300 mg/L of casein, 68.5 g/L of sucrose, 36 g/L of glucose, 40 mg/L of Acetosyringone (AS), 1 mg/L of 2,4-dichlorophenoxyacetic acid (2,4-D), pH=5.3)) to initiate the inoculation. Young embryo and Agrobacterium were cocultivated for a period (3 days) (Step 2: co-cultivation step). Preferably, the Young embryo was cultivated on a solid medium (4.3 g/L of MS salt, MS vitamins, 300 mg/L of casein, 20 g/L of sucrose, 10 g/L of glucose, 100 mg/L of Acetosyringone (AS), 1 mg/L of 2,4-dichlorophenoxyacetic acid (2,4-D) and 8 g/L of Agar, pH=5.8) after the infection step. After this cocultivation step, a selective "recovery" step can be preceded. In the "recovery" step, the recovery medium (4.3 g/L of MS salt, MS vitamins, 300 mg/L of casein, 30 g/L of sucrose, 1 mg/L of 2,4-dichlorophenoxyacetic acid (2,4-D)

and 3 g/L of phytagel, pH=5.8) contains at least one kind of known *Agrobacterium*-inhibiting antibiotics (cephalosporin) without the selective agent for plant transfectants (Step 3: recovery step). Preferably, the young embryo was cultivated on a solid medium culture containing antibiotics but without selective agent so as to eliminate *Agrobacterium* and to provide a recovery period for the infected cells. Then, the inoculated young embryo was cultivated on a medium containing selective agent (mannose) and the transformed, growing callus was selected (Step 4: selection step). Preferably, the young embryo was cultivated on a selective solid medium containing selective agent (4.3 g/L of MS salt, MS vitamins, 300 mg/L of casein, 30 g/L of sucrose, 12.5 g/L of mannose, 1 mg/L of 2,4-dichlorophenoxyacetic acid (2,4-D) and 3 g/L of phytagel, pH=5.8), resulting the selective growth of the transformed cells. Then, callus regenerated into plants (Step 5: regeneration step). Preferably, the callus was cultivated on a solid medium containing selective agent (MS differentiation medium and MS rooting medium) to regenerate into plants.

The obtained resistant callus was transferred to said MS differentiation medium (4.3 g/L MS salt, MS vitamins, 300 mg/L of casein, 30 g/L of sucrose, 2 mg/L of 6-benzyladenine, 5 g/L of mannose and 3 g/L phytagel, pH=5.8) and cultivated and differentiated at 25° C. The differentiated seedlings were transferred to said MS rooting medium (2.15 g/L of MS salt, MS vitamins, 300 mg/L of casein, 30 g/L of sucrose, 1 mg/L indole-3-acetic acid and 3 g/L phytagel, pH=5.8) and cultivated to about 10 cm in height at 25° C. Next, the seedlings were transferred to and cultivated in the greenhouse until fructification. In the greenhouse, the corn plants were cultivated at 28° C. for 16 hours and at 20° C. for 8 hours every day.

2. Verification of Transgenic Corn Plants with Inserted 24DT21 Gene Using TaqMan Technique 100 mg of leaves from every transformed corn plant (corn plant transformed with 24DT21 nucleotide sequence or control nucleotide sequence, respectively) was taken as sample respectively. Genomic DNA thereof was extracted using DNeasy Plant Maxi Kit (Qiagen) and the copy number of PMI gene was quantified through Taqman probe-based fluorescence quantitative PCR assay in order to determine the copy number of 24DT21. Wild type corn plant was taken as a control and analyzed according to the processes as described above. Experiments were carried out in triplicate and the results were the mean values.

The specific method for detecting the copy number of PMI gene was described as follows:

Step 31: 100 mg of leaves from every transformed corn plant (corn plant transformed with 24DT21 nucleotide sequence or control nucleotide sequence, respectively) and wild type corn plant was taken and grinded into homogenate in a mortar in liquid nitrogen respectively. It was in triplicate for each sample;

Step 32: the genomic DNAs of the samples above were extracted using DNeasy Plant Mini Kit (Qiagen) following the product instruction thereof;

Step 33: the genome DNA concentrations of the above samples were determined using NanoDrop 2000 (Thermo Scientific);

Step 34: the genome DNA concentrations were adjusted to the same range of 80-100 ng/µl;

Step 35: the copy numbers of the samples were quantified using Taqman probe-based fluorescence quantitative PCR assay, the quantified sample with known copy number was taken as a standard sample and the wild type corn plant was taken as a control. It was carried out in triplicate for every sample and the results were the mean values. Primers and the probes used in the fluorescence quantitative PCR were shown as below:

The following primers and probes are used to detect the PMI nucleotide sequence:

```
Primer 3:
GCTGTAAGAGCTTACTGAAAAAATTAACA
as shown in SEQ ID NO: 14 in the sequence list;

Primer 4:
CGATCTGCAGGTCGACGG
as shown in SEQ ID NO: 15 in the sequence list;

Probe 2:
TCTCTTGCTAAGCTGGGAGCTCGATCC
as shown in SEQ ID NO: 16 in the sequence list;
```

PCR Reaction System:

| | |
|---|---|
| JumpStart ™ Taq ReadyMix ™ (Sigma) | 10 µL |
| 50 × primer/probe mixture | 1 µL |
| Genome DNA | 3 µL |
| Water (ddH$_2$O) | 6 µL |

The 50× primer/probe mixture containing 45 µL of each primer (1 mM), 50 µL of the probe (100 µM) and 860 µL of 1 xTE buffer and was stored in an amber tube at 4° C.

PCR Reaction Conditions:

| Step | Temperature | Time |
|---|---|---|
| 41 | 95° C. | 5 min |
| 42 | 95° C. | 30 s |
| 43 | 60° C. | 1 min |
| 44 | Back to Step 42, repeat 40 times | |

Use the SDS2.3 Software (Applied Biosystems) to Analyze Data.

The experimental results showed that all the nucleotide sequences of 24DT21 nucleotide sequence and the control nucleotide sequence have been integrated into the genomes of the detected corn plants, respectively. Furthermore, all corn plants transformed 24DT21 nucleotide sequence and the control nucleotide sequence respectively contained single copy of 24DT21 gene.

Example 9: Herbicide-Resistance Effect Tests of the Transgenic Corn Plants

Herbicide resistance effects tests to 2,4-D dimethyl ammonium salt and agroxone of corn plants containing 24DT21 nucleotide sequence, control nucleotide sequence respectively and wild type corn plants (stages V3-V4) were performed respectively.

Corn plants containing 24DT21 nucleotide sequence, control nucleotide sequence respectively and wild type corn plants were taken and spayed with 2,4-D dimethyl ammonium salt (8960 g ae/ha, 16-folds concentration in field), agroxone (8960 g ae/ha, 16-folds concentration in field) and blank solvent (water) respectively. Prop root development was counted 21 days after spaying. Three strains (S6, S7 and S8) of corn plants transformed with 24DT21 nucleotide sequence, two strains (S9 and S10) of corn plants transformed with control nucleotide sequence and 1 strain of wild type (CK2) corn were selected and 10-15 plants from each stain were tested. The results were shown in Table 3.

TABLE 3

Results of herbicide-resistance effect tests of the transgenic corn T1 plants

| Treatment | Corn genotype | Normal development of brace roots | Abnormal development of brace roots | Proportion of normal development of brace roots |
|---|---|---|---|---|
| Blank solvent (Water) | S6 | 10 | 0 | 100.00% |
|  | S7 | 13 | 0 | 100.00% |
|  | S8 | 14 | 0 | 100.00% |
|  | S9 | 12 | 0 | 100.00% |
|  | S10 | 10 | 0 | 100.00% |
|  | CK2 | 15 | 0 | 100.00% |
| 8960 g ae/ha 2,4-D dimethyl ammonium salt (16 × 2,4-D) | S6 | 12 | 0 | 100.00% |
|  | S7 | 13 | 0 | 100.00% |
|  | S8 | 11 | 0 | 100.00% |
|  | S9 | 0 | 12 | 0% |
|  | S10 | 0 | 11 | 0% |
|  | CK2 | 0 | 15 | 0% |
| 8960 g ae/ha agroxone (16 × MCPA) | S6 | 11 | 0 | 100.00% |
|  | S7 | 12 | 0 | 100.00% |
|  | S8 | 13 | 0 | 100.00% |
|  | S9 | 0 | 13 | 0% |
|  | S10 | 0 | 10 | 0% |
|  | CK2 | 0 | 15 | 0% |

Results in Table 3 indicated that the 24DT21 gene conferred high resistance against herbicides to the transgenic corn plants, especially the phenoxy auxin herbicides (since the monocotyledon plants inherently have certain resistance to phenoxy auxin herbicides, high levels of resistance appeared); while none of the wild type of corn plants and the corn plants transformed with control sequences showed high levels of resistance against herbicides.

Above all, corn, soybean and *Arabidopsis thaliana* plants transformed with 24DT21 nucleotide sequence had high herbicide-resistance ability. Preferred codons of plant were employed in the herbicide-resistant gene 24DT21 in present invention, resulting that the herbicide-resistant gene of present invention is suitable to be expressed in plants. 24DT21 herbicide-resistant protein of present invention has a broad herbicide-resistance spectrum, especially phenoxy auxin herbicides.

Finally what should be explained is that all the above examples are merely intentioned to illustrate the technical solutions of present invention rather than to restrict present invention. Although detailed description of this invention has been provided by referring to the preferable examples, one skilled in the art should understand that the technical solutions of the invention can be modified or equivalently substituted while still fall within the spirit and scope of the present invention.

What is claimed is:

1. A herbicide-resistant protein, comprising:
a protein consisting of an amino acid sequence shown in SEQ ID NO: 2.

2. A herbicide-resistant gene, comprising:
(a) a nucleotide sequence encoding the herbicide-resistant protein according to claim 1; or
(b) a nucleotide sequence that is fully complementary to the nucleotide sequence as defined in (a); or
(c) a nucleotide sequence set forth in SEQ ID NO: 1.

3. A method for extending the target range of herbicides, comprising co-expressing said herbicide-resistant protein of claim 1 in a plant with at least a second nucleotide sequence encoding a protein which is different from said herbicide-resistant protein.

4. The method of claim 3, wherein said second nucleotide sequence encodes a glyphosate-resistant protein, a glufosinate ammonium resistant protein, 4-hydroxyphenylpyruvic acid dioxygenase, acetolactate synthase, cytochrome protein or protoporphyrinogen oxidase.

5. A method for selecting transformed plant cells comprising the steps of transforming multiple plant cells with a nucleotide sequence encoding said herbicide-resistant protein of claim 1, and cultivating said cells at a phenoxy auxin herbicide concentration which allows the growth of the transformed cells expressing said nucleotide sequence encoding said herbicide-resistant protein while killing the un-transformed cells or inhibiting the growth of the un-transformed cells.

6. The method of claim 5, wherein said plant is selected from the group consisting of soybean, cotton, corn, rice, wheat, beet and sugarcane.

7. The method of claim 5, wherein said phenoxy auxin herbicide includes 2,4-D or MCPA.

8. A method for controlling weeds, comprising applying an effective amount of one or more herbicides to the field planted with plants comprising a nucleotide sequence encoding said herbicide-resistant protein of claim 1.

9. The method of claim 8, wherein said plants are selected from the group consisting of soybean, cotton, corn, rice, wheat, beet and sugarcane.

10. The method of claim 8, wherein said plants are also tolerant to glyphosate herbicide.

11. The method of claim 10, wherein said herbicides at least include phenoxy auxin and glyphosate.

12. The method of claim 11, wherein said phenoxy auxin herbicides include 2,4-D or MCPA.

13. A method for protecting plants from the damage caused by herbicides comprising introducing a nucleotide sequence encoding said herbicide-resistant protein of claim 1 into the plants, so as to make the resulted plants produce a certain quantity of said herbicide-resistant protein sufficient to protect them from the damage caused by phenoxy auxin herbicides.

14. The method of claim 13, wherein said plants are selected from the group consisting of soybean, cotton, corn, rice, wheat, beet and sugarcane.

15. The method of claim 13, wherein said phenoxy auxin herbicides include 2,4-D or MCPA.

16. A method for conferring plants with resistance to herbicides comprising the step of introducing a polynucleotide into the plants, wherein the polynucleotide comprises a nucleotide sequence encoding said herbicide-resistant protein of claim 1.

17. The method of claim 16, wherein said plants are selected from the group consisting of soybean, cotton, corn, rice, wheat, beet and sugarcane.

18. The method of claim 16, wherein the herbicides include 2,4-D or MCPA.

* * * * *

SEQUENCE LISTING

<160> NUMBER OF SEQ ID NOS: 16

<210> SEQ ID NO 1
<211> LENGTH: 879
<212> TYPE: DNA
<213> ORGANISM: Artificial Sequence
<220> FEATURE:
<223> OTHER INFORMATION: Artificial 24DT21 nucleotide sequence

<400> SEQUENCE: 1

```
atgagcccg cttttgacat agccccactc gacgcaactt ttggcgcagt cgttacaggc      60
gttcacctcg caactttgga tgatgccgga ttcgccgctc ttcacgcagc gtggttgcag     120
catgctctcc tgattttcc cggacaacac ctgagtaacg atcagcaaat cacattcgca     180
aagaggtttg gtgcgattga gcgcatcggc ggaggcgata tagtggcaat tagtaacgtt     240
aaggcagacg gaacggttag gcagcactcg ccagccgaat gggatgacat gatgaaagtc     300
atagtgggga atatggcctg gcatgctgat tccacataca tgcccgtcat ggcacaaggc     360
gcggtgttct ctgcagaggt ggttccagct gtcggaggca gaacctgctt tgccgacatg     420
cgggccgctt acgatgctct cgacgaagcc actagggctc tggtgcacca gaggagcgcc     480
cgccattcac ttgtttattc ccaatctaag ttggggcacg tccagcaagc aggctctgcg     540
tacatcggat atggtatgga taccactgcc acaccacttc gcccttttggt taaagtccat     600 ccagagactg gaaggccgag ccttttgatc ggtcgccacg cacatgcgat accagggatg     660
```

```
gatgcagcgg agtcagaaag attcctcgaa ggcctggtgg actgggcatg ccaggctcct    720
cgggttcacg cacatcaatg ggccgctggc gatgtcgtgg tttgggacaa tagatgtctc    780
ctgcatcggg ctgagccatg ggactttaaa ctccctagag ttatgtggca ttcaaggata    840
gcgggcgacc cagcgtcaga aacagcactc gctcattga                           879
```

<210> SEQ ID NO 2
<211> LENGTH: 292
<212> TYPE: PRT
<213> ORGANISM: Artificial Sequence
<220> FEATURE:
<223> OTHER INFORMATION: Artificial 24DT21 amino sequence

<400> SEQUENCE: 2

```
Met Ser Pro Ala Phe Asp Ile Ala Pro Leu Asp Ala Thr Phe Gly Ala
1               5                   10                  15

Val Val Thr Gly Val His Leu Ala Thr Leu Asp Asp Ala Gly Phe Ala
            20                  25                  30

Ala Leu His Ala Ala Trp Leu Gln His Ala Leu Leu Ile Phe Pro Gly
        35                  40                  45

Gln His Leu Ser Asn Asp Gln Gln Ile Thr Phe Ala Lys Arg Phe Gly
    50                  55                  60

Ala Ile Glu Arg Ile Gly Gly Gly Asp Ile Val Ala Ile Ser Asn Val
65                  70                  75                  80

Lys Ala Asp Gly Thr Val Arg Gln His Ser Pro Ala Glu Trp Asp Asp
                85                  90                  95

Met Met Lys Val Ile Val Gly Asn Met Ala Trp His Ala Asp Ser Thr
            100                 105                 110

Tyr Met Pro Val Met Ala Gln Gly Ala Val Phe Ser Ala Glu Val Val
        115                 120                 125

Pro Ala Val Gly Gly Arg Thr Cys Phe Ala Asp Met Arg Ala Ala Tyr
    130                 135                 140

Asp Ala Leu Asp Glu Ala Thr Arg Ala Leu Val His Gln Arg Ser Ala
145                 150                 155                 160

Arg His Ser Leu Val Tyr Ser Gln Ser Lys Leu Gly His Val Gln Gln
                165                 170                 175

Ala Gly Ser Ala Tyr Ile Gly Tyr Gly Met Asp Thr Thr Ala Thr Pro
            180                 185                 190

Leu Arg Pro Leu Val Lys Val His Pro Glu Thr Gly Arg Pro Ser Leu
        195                 200                 205

Leu Ile Gly Arg His Ala His Ala Ile Pro Gly Met Asp Ala Ala Glu
    210                 215                 220

Ser Glu Arg Phe Leu Glu Gly Leu Val Asp Trp Ala Cys Gln Ala Pro
225                 230                 235                 240

Arg Val His Ala His Gln Trp Ala Ala Gly Asp Val Val Trp Asp
                245                 250                 255

Asn Arg Cys Leu Leu His Arg Ala Glu Pro Trp Asp Phe Lys Leu Pro
            260                 265                 270

Arg Val Met Trp His Ser Arg Ile Ala Gly Asp Pro Ala Ser Glu Thr
        275                 280                 285

Ala Leu Ala His
    290
```

<210> SEQ ID NO 3
<211> LENGTH: 1322
<212> TYPE: DNA
<213> ORGANISM: Arabidopsis thaliana

<400> SEQUENCE: 3

```
gtcgacctgc aggtcaacgg atcaggatat tcttgtttaa gatgttgaac tctatggagg    60
tttgtatgaa ctgatgatct aggaccggat aagttccctt cttcatagcg aacttattca   120
aagaatgttt tgtgtatcat tcttgttaca ttgttattaa tgaaaaaata ttattggtca   180
ttggactgaa cacgagtgtt aaatatggac caggccccaa ataagatcca ttgatatatg   240
aattaaataa caagaataaa tcgagtcacc aaaccacttg cctttttaa cgagacttgt    300
tcaccaactt gatacaaaag tcattatcct atgcaaatca ataatcatac aaaaatatcc   360
aataacacta aaaattaaa agaaatggat aatttcacaa tatgttatac gataaagaag    420
ttacttttcc aagaaattca ctgattttat aagcccactt gcattagata aatggcaaaa   480
aaaacaaaa aggaaaagaa ataagcacg aagaattcta gaaaatacga aatacgcttc     540
aatgcagtgg gacccacggt tcaattattg ccaattttca gctccaccgt atatttaaaa   600
aataaaacga taatgctaaa aaaatataaa tcgtaacgat cgttaaatct caacggctgg   660
atcttatgac gaccgttaga aattgtggtt gtcgacgagt cagtaataaa cggcgtcaaa   720
gtggttgcag ccggcacaca cgagtcgtgt ttatcaactc aaagcacaaa tacttttcct   780
caacctaaaa ataaggcaat tagccaaaaa caactttgcg tgtaaacaac gctcaataca   840
cgtgtcattt tattattagc tattgcttca ccgccttagc tttctcgtga cctagtcgtc   900
ctcgtctttt cttcttcttc ttctataaaa caatacccaa agcttcttct tcacaattca   960
gatttcaatt tctcaaaatc ttaaaaactt tctctcaatt ctctctaccg tgatcaaggt  1020
aaatttctgt gttccttatt ctctcaaaat cttcgatttt gttttcgttc gatcccaatt  1080
tcgtatatgt tctttggttt agattctgtt aatcttagat cgaagacgat tttctgggtt  1140
tgatcgttag atatcatctt aattctcgat tagggtttca taaatatcat ccgatttgtt  1200
caaataattt gagttttgtc gaataattac tcttcgattt gtgatttcta tctagatctg  1260
gtgttagttt ctagtttgtg cgatcgaatt tgtcgattaa tctgagtttt tctgattaac  1320
ag                                                                 1322
```

<210> SEQ ID NO 4
<211> LENGTH: 253
<212> TYPE: DNA
<213> ORGANISM: Agrobacterium tumefaciens

<400> SEQUENCE: 4

```
gatcgttcaa acatttggca ataaagtttc ttaagattga atcctgttgc cggtcttgcg    60
atgattatca tataatttct gttgaattac gttaagcatg taataattaa catgtaatgc   120
atgacgttat ttatgagatg ggtttttatg attagagtcc cgcaattata catttaatac   180
gcgatagaaa acaaaatata gcgcgcaaac taggataaat tatcgcgcgc ggtgtcatct   240
atgttactag atc                                                      253
```

<210> SEQ ID NO 5
<211> LENGTH: 530
<212> TYPE: DNA
<213> ORGANISM: Cauliflower mosaic virus

<400> SEQUENCE: 5

```
ccatggagtc aaagattcaa atagaggacc taacagaact cgccgtaaag actggcgaac      60
agttcataca gagtctctta cgactcaatg acaagaagaa aatcttcgtc aacatggtgg     120
agcacgacac gcttgtctac tccaaaaata tcaaagatac agtctcagaa gaccaaaggg     180
caattgagac ttttcaacaa agggtaatat ccggaaacct cctcggattc cattgcccag     240
ctatctgtca ctttattgtg aagatagtgg aaaaggaagg tggctcctac aaatgccatc     300
attgcgataa aggaaaggcc atcgttgaag atgcctctgc cgacagtggt cccaaagatg     360
gaccccccacc cacgaggagc atcgtggaaa agaagacgt tccaaccacg tcttcaaagc     420
aagtggattg atgtgatatc tccactgacg taagggatga cgcacaatcc cactatcctt     480
cgcaagaccc ttcctctata taaggaagtt catttcattt ggagaggaca                 530
```

<210> SEQ ID NO 6
<211> LENGTH: 552
<212> TYPE: DNA
<213> ORGANISM: Streptomyces viridochromogenes

<400> SEQUENCE: 6

```
atgtctccgg agaggagacc agttgagatt aggccagcta cagcagctga tatggccgcg      60
gtttgtgata tcgttaacca ttacattgag acgtctacag tgaactttag gacagagcca     120
caaacaccac aagagtggat tgatgatcta gagaggttgc aagatagata cccttggttg     180
gttgctgagg ttgagggtgt tgtggctggt attgcttacg ctgggccctg gaaggctagg     240
aacgcttacg attggacagt tgagagtact gtttacgtgt cacataggca tcaaaggttg     300
ggcctaggat ccacattgta cacacatttg cttaagtcta tggaggcgca aggttttaag     360
tctgtggttg ctgttatagg ccttccaaac gatccatctg ttaggttgca tgaggctttg     420
ggatacacag cccggggtac attgcgcgca gctggataca agcatggtgg atggcatgat     480
gttggttttt ggcaaaggga ttttgagttg ccagctcctc caaggccagt taggccagtt     540
acccagatct ga                                                          552
```

<210> SEQ ID NO 7
<211> LENGTH: 195
<212> TYPE: DNA
<213> ORGANISM: Cauliflower mosaic virus

<400> SEQUENCE: 7

```
ctgaaatcac cagtctctct ctacaaatct atctctctct ataataatgt gtgagtagtt      60
cccagataag ggaattaggg ttcttatagg gtttcgctca tgtgttgagc atataagaaa     120
cccttagtat gtatttgtat ttgtaaaata cttctatcaa taaaatttct aattcctaaa     180
accaaaatcc agtgg                                                       195
```

<210> SEQ ID NO 8
<211> LENGTH: 1848
<212> TYPE: DNA
<213> ORGANISM: Artificial Sequence
<220> FEATURE:
<223> OTHER INFORMATION: Artificial control sequence

<400> SEQUENCE: 8

```
atggacaaca acccaaacat caacgaatgc attccataca actgcttgag taacccagaa      60
gttgaagtac ttggtggaga acgcattgaa accggttaca ctcccatcga catctccttg     120
tccttgacac agtttctgct cagcgagttc gtgccaggtg ctgggttcgt tctcggacta     180
```

```
gttgacatca tctggggtat ctttggtcca tctcaatggg atgcattcct ggtgcaaatt    240
gagcagttga tcaaccagag gatcgaagag ttcgccagga accaggccat ctctaggttg    300
gaaggattga gcaatctcta ccaaatctat gcagagagct tcagagagtg ggaagccgat    360
cctactaacc cagctctccg cgaggaaatg cgtattcaat tcaacgacat gaacagcgcc    420
ttgaccacag ctatcccatt gttcgcagtc cagaactacc aagttcctct cttgtccgtg    480
tacgttcaag cagctaatct tcacctcagc gtgcttcgag acgttagcgt gtttgggcaa    540
aggtggggat tcgatgctgc aaccatcaat agccgttaca acgaccttac taggctgatt    600
ggaaactaca ccgaccacgc tgttcgttgg tacaacactg gcttggagcg tgtctggggt    660
cctgattcta gagattggat tagatacaac cagttcagga gagaattgac cctcacagtt    720
ttggacattg tgtctctctt cccgaactat gactccagaa cctaccctat ccgtacagtg    780
tcccaactta ccagagaaat ctatactaac ccagttcttg agaacttcga cggtagcttc    840
cgtggttctg cccaaggtat cgaaggctcc atcaggagcc cacacttgat ggacatcttg    900
aacagcataa ctatctacac cgatgctcac agaggagagt attactggtc tggacaccag    960
atcatggcct ctccagttgg attcagcggg cccgagttta cctttcctct ctatggaact   1020
atgggaaacg ccgctccaca caacgtatc gttgctcaac taggtcaggg tgtctacaga   1080
accttgtctt ccaccttgta cagaagaccc ttcaatatcg gtatcaacaa ccagcaactt   1140
tccgttcttg acgaacaga gttcgcctat ggaacctctt ctaacttgcc atccgctgtt   1200
tacagaaaga gcggaaccgt tgattccttg gacgaaatcc caccacagaa caacaatgtg   1260
ccacccaggc aaggattctc ccacaggttg agccacgtgt ccatgttccg ttccggattc   1320
agcaacagtt ccgtgagcat catcagagct cctatgttct catggattca tcgtagtgct   1380
gagttcaaca atatcattcc ttcctctcaa atcacccaaa tcccattgac caagtctact   1440
aaccttggat ctggaacttc tgtcgtgaaa ggaccaggct tcacaggagg tgatattctt   1500
agaagaactt ctcctggcca gattagcacc ctcagagtta acatcactgc accactttct   1560
caaagatatc gtgtcaggat tcgttacgca tctaccacta acttgcaatt ccacacctcc   1620
atcgacggaa ggcctatcaa tcagggtaac ttctccgcaa ccatgtcaag cggcagcaac   1680
ttgcaatccg gcagcttcag aaccgtcggt ttcactactc ctttcaactt ctctaacgga   1740
tcaagcgttt tcacccttag cgctcatgtg ttcaattctg gcaatgaagt gtacattgac   1800
cgtattgagt ttgtgcctgc cgaagttacc ttcgaggctg agtactga                1848

<210> SEQ ID NO 9
<211> LENGTH: 1992
<212> TYPE: DNA
<213> ORGANISM: Zea mays

<400> SEQUENCE: 9
ctgcagtgca gcgtgacccg gtcgtgcccc tctctagaga taatgagcat tgcatgtcta     60
agttataaaa aattaccaca tattttttt gtcacacttg tttgaagtgc agtttatcta    120
tctttataca tatatttaaa ctttactcta cgaataatat aatctatagt actacaataa    180
tatcagtgtt ttagagaatc atataaatga acagttagac atggtctaaa ggacaattga    240
gtattttgac aacaggactc tacagtttta tcttttagt gtgcatgtgt tctccttttt    300
ttttgcaaat agcttcacct atataatact tcatccattt tattagtaca tccatttagg    360
gtttagggtt aatggttttt atagactaat ttttttagta catctatttt attctatttt    420
agcctctaaa ttaagaaaac taaaactcta ttttagtttt tttatttaat aatttagata    480
```

-continued

```
taaaatagaa taaaataaag tgactaaaaa ttaaacaaat acccttttaag aaattaaaaa      540 aactaaggaa acattttttct tgtttcgagt agataatgcc agcctgttaa acgccgtcga      600
cgagtctaac ggacaccaac cagcgaacca gcagcgtcgc gtcgggccaa gcgaagcaga      660
cggcacggca tctctgtcgc tgcctctgga cccctctcga gagttccgct ccaccgttgg      720
acttgctccg ctgtcggcat ccagaaattg cgtggcggag cggcagacgt gagccggcac      780
ggcaggcggc ctcctcctcc tctcacggca cggcagctac gggggattcc tttcccaccg      840
ctccttcgct ttcccttcct cgcccgccgt aataaataga caccccctcc acaccctctt      900
tccccaacct cgtgttgttc ggagcgcaca cacacacaac cagatctccc ccaaatccac      960
ccgtcggcac ctccgcttca aggtacgccg ctcgtcctcc ccccccccc ctctctacct      1020 tctctagatc ggcgttccgg tccatggtta gggcccggta gttctacttc tgttcatgtt      1080
tgtgttagat ccgtgtttgt gttagatccg tgctgctagc gttcgtacac ggatgcgacc      1140
tgtacgtcag acacgttctg attgctaact tgccagtgtt tctctttggg gaatcctggg      1200
atggctctag ccgttccgca gacgggatcg atttcatgat ttttttttgtt tcgttgcata      1260 gggtttggtt tgccctttc ctttatttca atatatgccg tgcacttgtt tgtcgggtca      1320
tcttttcatg ctttttttg tcttggttgt gatgatgtgg tctggttggg cggtcgttct      1380
agatcggagt agaattctgt ttcaaactac ctggtggatt tattaatttt ggatctgtat      1440
gtgtgtgcca tacatattca tagttacgaa ttgaagatga tggatggaaa tatcgatcta      1500
ggataggtat acatgttgat gcgggttta ctgatgcata tacagagatg ctttttgttc      1560
gcttggttgt gatgatgtgg tgtgttggg cggtcgttca ttcgttctag atcggagtag      1620
aatactgttt caaactacct ggtgtattta ttaatttgg aactgtatgt gtgtgtcata      1680
catcttcata gttacgagtt taagatggat ggaaatatcg atctaggata ggtatacatg      1740
ttgatgtggg ttttactgat gcatatacat gatggcatat gcagcatcta ttcatatgct      1800
ctaaccttga gtacctatct attataataa acaagtatgt tttataatta ttttgatctt      1860
gatatacttg gatgatggca tatgcagcag ctatatgtgg attttttttag ccctgccttc      1920 atacgctatt tatttgcttg gtactgtttc ttttgtcgat gctcaccctg ttgtttggtg      1980
ttacttctgc ag                                                          1992
```

<210> SEQ ID NO 10
<211> LENGTH: 1176
<212> TYPE: DNA
<213> ORGANISM: Escherichia coli

<400> SEQUENCE: 10

```
atgcaaaaac tcattaactc agtgcaaaac tatgcctggg gcagcaaaac ggcgttgact       60
gaactttatg gtatggaaaa tccgtccagc cagccgatgg ccgagctgtg gatgggcgca      120
catccgaaaa gcagttcacg agtgcagaat gccgccggag atatcgtttc actgcgtgat      180
gtgattgaga gtgataaatc gactctgctc ggagaggccg ttgccaaacg ctttggcgaa      240
ctgcctttcc tgttcaaagt attatgcgca gcacagccac tctccattca ggttcatcca      300
aacaaacaca attctgaaat cggttttgcc aaagaaaatg ccgcaggtat cccgatggat      360
gccgccgagc gtaactataa agatcctaac cacaagccgg agctggtttt tgcgctgacg      420
cctttccttg cgatgaacgc gtttcgtgaa ttttccgaga ttgtctccct actccagccg      480
gtcgcaggtg cacatccggc gattgctcac tttttacaac agcctgatgc cgaacgttta      540
```

```
agcgaactgt tcgccagcct gttgaatatg cagggtgaag aaaaatcccg cgcgctggcg      600
attttaaaat cggccctcga tagccagcag ggtgaaccgt ggcaaacgat tcgtttaatt      660
tctgaatttt acccggaaga cagcggtctg ttctccccgc tattgctgaa tgtggtgaaa      720
ttgaaccctg gcgaagcgat gttcctgttc gctgaaacac cgcacgctta cctgcaaggc      780
gtggcgctgg aagtgatggc aaactccgat aacgtgctgc gtgcgggtct gacgcctaaa      840
tacattgata ttccggaact ggttgccaat gtgaaattcg aagccaaacc ggctaaccag      900
ttgttgaccc agccggtgaa acaaggtgca gaactggact cccgattcc agtggatgat       960 tttgccttct cgctgcatga ccttagtgat aaagaaacca ccattagcca gcagagtgcc     1020
gccattttgt tctgcgtcga aggcgatgca acgttgtgga aaggttctca gcagttacag     1080
cttaaaccgg gtgaatcagc gtttattgcc gccaacgaat caccggtgac tgtcaaaggc     1140
cacggccgtt tagcgcgtgt ttacaacaag ctgtaa                               1176
```

<210> SEQ ID NO 11
<211> LENGTH: 22
<212> TYPE: DNA
<213> ORGANISM: Artificial Sequence
<220> FEATURE:
<223> OTHER INFORMATION: Artificial oligonucleotide primer 1

<400> SEQUENCE: 11
gagggtgttg tggctggtat tg                                              22

<210> SEQ ID NO 12
<211> LENGTH: 23
<212> TYPE: DNA
<213> ORGANISM: Artificial Sequence
<220> FEATURE:
<223> OTHER INFORMATION: primer2

<400> SEQUENCE: 12
tctcaactgt ccaatcgtaa gcg                                             23

<210> SEQ ID NO 13
<211> LENGTH: 25
<212> TYPE: DNA
<213> ORGANISM: Artificial Sequence
<220> FEATURE:
<223> OTHER INFORMATION: Artificial oligonucleotide probe 1

<400> SEQUENCE: 13
cttacgctgg gccctggaag gctag                                           25

<210> SEQ ID NO 14
<211> LENGTH: 29
<212> TYPE: DNA
<213> ORGANISM: Artificial Sequence
<220> FEATURE:
<223> OTHER INFORMATION: Artificial oligonucleotide primer 3

<400> SEQUENCE: 14
gctgtaagag cttactgaaa aaattaaca                                       29

<210> SEQ ID NO 15
<211> LENGTH: 18
<212> TYPE: DNA
<213> ORGANISM: Artificial Sequence
<220> FEATURE:
<223> OTHER INFORMATION: Artificial oligonucleotide primer 4

```
<400> SEQUENCE: 15
cgatctgcag gtcgacgg                                                         18

<210> SEQ ID NO 16
<211> LENGTH: 27
<212> TYPE: DNA
<213> ORGANISM: Artificial Sequence
<220> FEATURE:
<223> OTHER INFORMATION: Artificial oligonucleotide probe 2

<400> SEQUENCE: 16
tctcttgcta agctgggagc tcgatcc                                               27
```